United States Patent
Tumlinson et al.

(10) Patent No.: US 10,809,050 B2
(45) Date of Patent: Oct. 20, 2020

(54) INTERFEROMETRY WITH PULSE BROADENED DIODE LASER

(71) Applicants: Carl Zeiss Meditec, Inc., Dublin, CA (US); Carl Zeiss Meditec AG, Jena (DE)

(72) Inventors: Alexandre R. Tumlinson, San Leandro, CA (US); Nathan Shemonski, San Francisco, CA (US); Yuan Liu, Dublin, CA (US)

(73) Assignees: CARL ZEISS MEDITEC, INC., Dublin, CA (US); CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 16/669,289

(22) Filed: Oct. 30, 2019

(65) Prior Publication Data

US 2020/0064117 A1   Feb. 27, 2020

Related U.S. Application Data

(63) Continuation of application No. 15/759,486, filed as application No. PCT/EP2016/071791 on Sep. 15, 2016, now Pat. No. 10,495,439.

(60) Provisional application No. 62/265,107, filed on Dec. 9, 2015, provisional application No. 62/219,872, filed on Sep. 17, 2015.

(51) Int. Cl.
*G01B 9/02* (2006.01)
*H01S 5/062* (2006.01)
*H01S 5/024* (2006.01)

(52) U.S. Cl.
CPC ..... *G01B 9/02004* (2013.01); *G01B 9/02014* (2013.01); *G01B 9/02044* (2013.01); *G01B 9/02047* (2013.01); *G01B 9/02091* (2013.01); *H01S 5/02407* (2013.01); *H01S 5/06216* (2013.01); *G01B 2290/20* (2013.01)

(58) Field of Classification Search
CPC ....... G01B 9/02; A61B 5/0066; A61B 5/6852; A61B 5/0073; G01N 21/4795
USPC ......................................................... 356/479
See application file for complete search history.

(56) References Cited

U.S. PATENT DOCUMENTS

| | | |
|---|---|---|
| 3,901,738 A | 8/1975 | Hunsperger et al. |
| 3,982,201 A | 9/1976 | Rosenkrantz et al. |
| 4,581,730 A | 4/1986 | Ozeki et al. |
| 5,181,214 A | 1/1993 | Berger et al. |
| 5,949,801 A | 9/1999 | Tayebati |
| 6,345,059 B1 | 2/2002 | Flanders |

(Continued)

OTHER PUBLICATIONS

Anderson et al., "3D-Spectral Imaging System for Anterior Chamber Metrology", Proceedings of SPIE, vol. 9312, Mar. 2, 2015, pp. 93120N-1-93120N-5.

(Continued)

*Primary Examiner* — Md M Rahman
(74) *Attorney, Agent, or Firm* — Morrison & Foerster LLP

(57) ABSTRACT

Various optical systems equipped with diode laser light sources are discussed in the present application. One example system includes a diode laser light source for providing a beam of radiation. The diode laser has a spectral output bandwidth when driven under equilibrium conditions. The system further includes a driver circuit to apply a pulse of drive current to the diode laser. The pulse causes a variation in the output wavelength of the diode laser during the pulse such that the spectral output bandwidth is at least two times larger the spectral output bandwidth under the equilibrium conditions.

8 Claims, 9 Drawing Sheets

(56) References Cited

U.S. PATENT DOCUMENTS

| | | |
|---|---|---|
| 6,882,431 B2 | 4/2005 | Teich et al. |
| 7,415,049 B2 | 8/2008 | Flanders et al. |
| 7,554,668 B2 | 6/2009 | Zhou et al. |
| 8,660,324 B2 | 2/2014 | Byren et al. |
| 9,373,933 B2 | 6/2016 | Njegovec et al. |
| 2005/0157303 A1 | 7/2005 | Langford et al. |
| 2006/0215716 A1 | 9/2006 | Luo et al. |
| 2014/0028974 A1 | 1/2014 | Tumlinson |
| 2014/0112361 A1 | 4/2014 | Njegovec et al. |
| 2014/0336957 A1 | 11/2014 | Hanson et al. |
| 2016/0285235 A1 | 9/2016 | Njegovec et al. |

OTHER PUBLICATIONS

Balboa et al., "Low-Coherence Optical Fibre Speckle Interferometry", Measurement Science and Technology, vol. 17, No. 4, Apr. 2006, pp. 1-18.

Bartl et al., "Tuning of the Laser Diode", Measurement Science Review, vol. 2, Section 3, 2002, pp. 9-15.

Bonin et al., "In Vivo Fourier-domain Full-field OCT of the Human Retina with 1.5 Million A-lines/s", Optics Letters, vol. 35, No. 20, Oct. 15, 2010, pp. 3432-3434.

Chen et al., "Short-Coherence-Length and High-Coupling-Efficiency Pulsed Diode Laser for Fiber-Optic Sensors", Optics Letters, vol. 13, No. 8, Aug. 1988, pp. 628-630.

Fechtig et al., "Line-Field Parallel Swept Source MHZ OCT for Structural and Functional Retinal Imaging", Biomedical Optics Express, vol. 6, No. 3, Mar. 1, 2015, pp. 716-735.

Feng et al., "Thermal Analysis of Gan Laser Diodes in a Package Structure", Chin. Phys. B., vol. 21, No. 8, 2012, pp. 084209-1-084209-6.

Girshovitz et al., "Doubling the Field of View in Off-Axis Low-Coherence Interferometric Imaging", Light: Science & Applications, vol. 3, 2014, pp. 1-9.

Grajciar et al., "Parallel Fourier Domain Optical Coherence Tomography for in Vivo Measurement of the Human Eye", Optics Express, vol. 13, No. 4, Feb. 21, 2005, pp. 1131-1137.

Haney et al., "Measurement of the Temporal Coherence Properties of Pulsed Single-mode Laser Diodes", Applied Optics, vol. 24, No. 13, Jul. 1, 1985, pp. 1926-1932.

Hergenroeder et al., "A Chirped Semiconductor Laser as an Alternative to the SLD in a Fiber Gyro", Optical Society of America, vol. 2, 1988, pp. 455-457.

Iftimia et al., "Dual-Beam Fourier Domain Optical Doppler Tomography of Zebrafish", Optics Express, vol. 16, No. 18, Sep. 1, 2008, pp. 13624-13636.

International Preliminary Report on Patentability received for PCT Patent Application No. PCT/EP2016/071791, dated Mar. 29, 2018, 11 pages.

International Search Report and Written Opinion received for PCT Patent Application No. PCT/EP2016/071791, dated Nov. 9, 2016, 13 pages.

Kobayashi et al., "Direct Frequency Modulation in AlGaAs Semiconductor Lasers", IEEE Journal of Quantum Electronics, vol. QE-18, No. 4, Apr. 1982, pp. 582-595.

Krstajic et al., "Tissue Surface as the Reference Arm in Fourier Domain Optical Coherence Tomography", Journal of Biomedical Optics, vol. 17, No. 7, Jul. 2012, pp. 071305-1-071305-6.

Meadows et al., "Thermal Characteristics of High-power Long-Pulsewidth Quasi-CW Laser Diode Arrays", Proceedings of SPIE—The International Society for Optical Engineering, Jun. 2004, 10 pages.

Nakamura et al., "High-Speed Three-dimensional Human Retinal Imaging by Line-Field Spectral Domain Optical Coherence Tomography", Optics Express, vol. 15, No. 12, Jun. 11, 2007, pp. 7103-7116.

Pache et al., "Fast Three-dimensional Imaging of Gold Nanoparticles in Living Cells with Photothermal Optical Lock-in Optical Coherence Microscopy", Optics Express, vol. 20, No. 19, Sep. 10, 2012, pp. 21385-21399.

Philippe et al., "Laser Diode Wavelength-modulation Spectroscopy for Simultaneous Measurement of Temperature, Pressure, and Velocity in Shock-heated Oxygen Flows", Applied Optics, vol. 32, No. 30, Oct. 20, 1993, pp. 6090-6103.

Sanders et al., "Rapid Temperature Tuning of a 1.4-µm Diode Laser with Application to High-pressure H2o Absorption Spectroscopy", Optics Letters, vol. 26, No. 20, Oct. 15, 2001, pp. 1568-1570.

Schmitt et al., "Speckle in Optical Coherence Tomography", Journal of Biomedical Optics, vol. 4, No. 1, Jan. 1999, pp. 95-105.

Shemonski et al., "Computational High-resolution Optical Imaging of the Living Human Retina", Nature Photonics, vol. 9, Jun. 22, 2015, 16 pages.

Suhir et al., "Modeling of Thermal Phenomena in a High-Power Diode Laser Package", International Conference on Electronic Packaging Technology & High-Density Packaging, Sep. 2009, 6 pages.

Wang et al., "Pulsed Laser Diode Optical Fiber Interferometer for Absolute Distance Measurement", Proceedings of SPIE, vol. 2839, Oct. 25, 1996, pp. 350-353.

Watanabe et al., "Full-field Optical Coherence Tomography by Achromatic Phase Shifting with a Rotating Polarizer", Applied Optics, vol. 44, No. 8, Mar. 10, 2005, pp. 1387-1392.

Yun et al., "Pulsed-source and Swept-source Spectral-domain Optical Coherence Tomography with Reduced Motion Artifacts", Optics Express, vol. 12, No. 23, Nov. 15, 2004, pp. 5614-5624.

Zeller et al., "High Power Pulsed 976 Nm DFB Laser Diodes", Proceedings of SPIE—The International Society for Optical Engineering, Apr. 2010, 10 pages.

Zhang et al., "Pulse Wavelength Scan of Room-temperature Mid-Infrared Distributed Feedback Quantum Cascade Lasers for N2o Gas Detection", Chinese Physics Letters, vol. 23, No. 7, 2006, pp. 1780-1783.

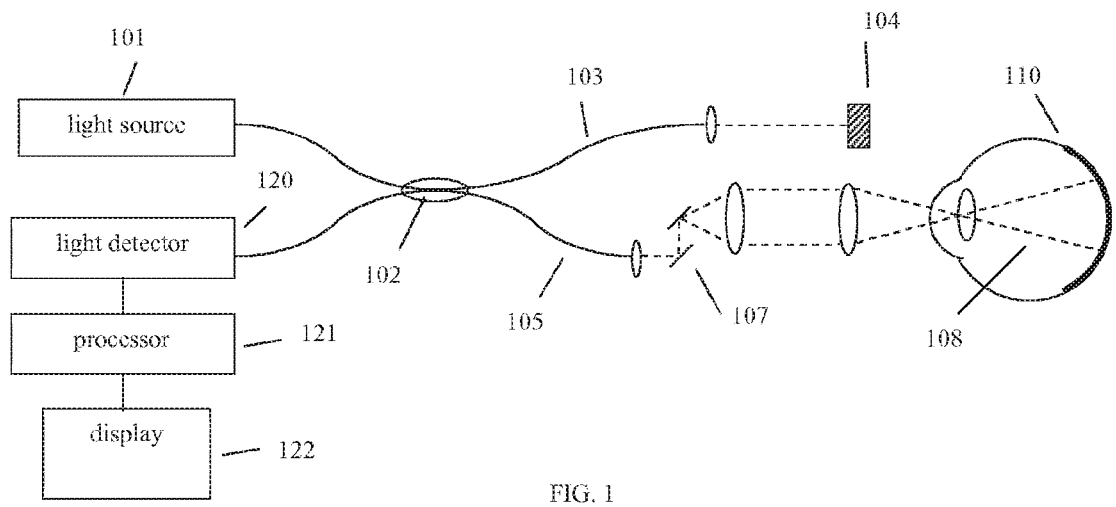
FIG. 1
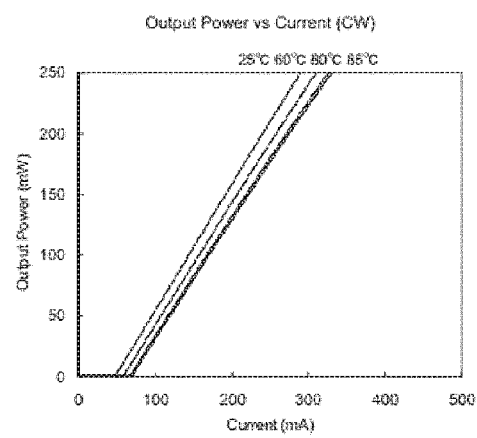
FIG. 2(a)
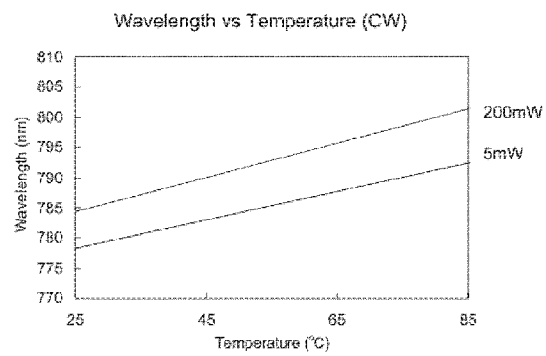
FIG. 2(b)
FIG. 2 (PRIOR ART)
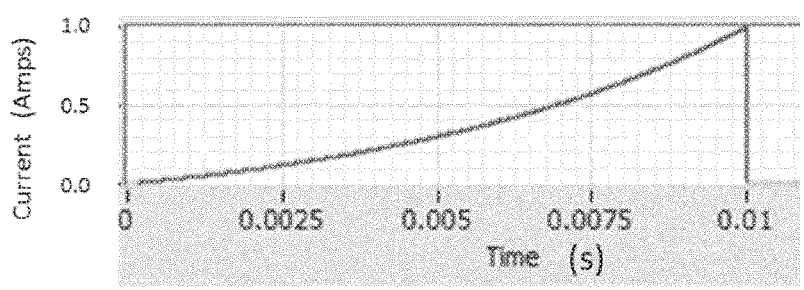
FIG. 3

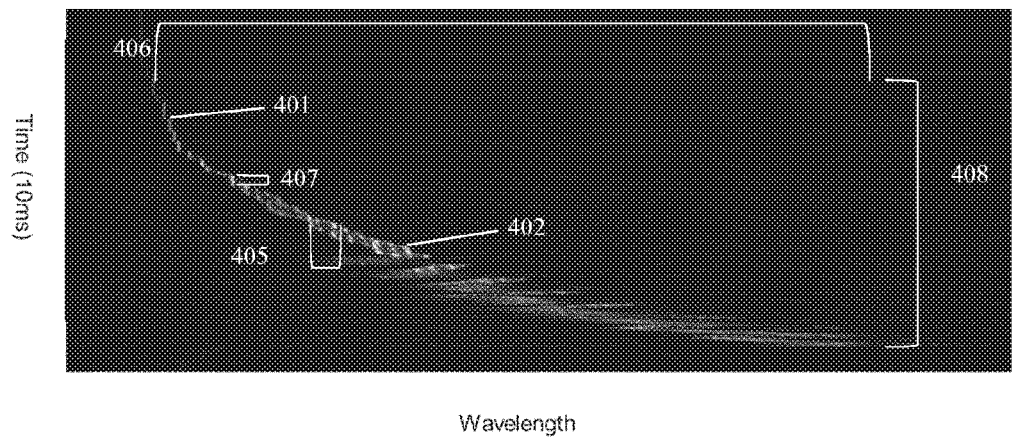
FIG. 4(a)
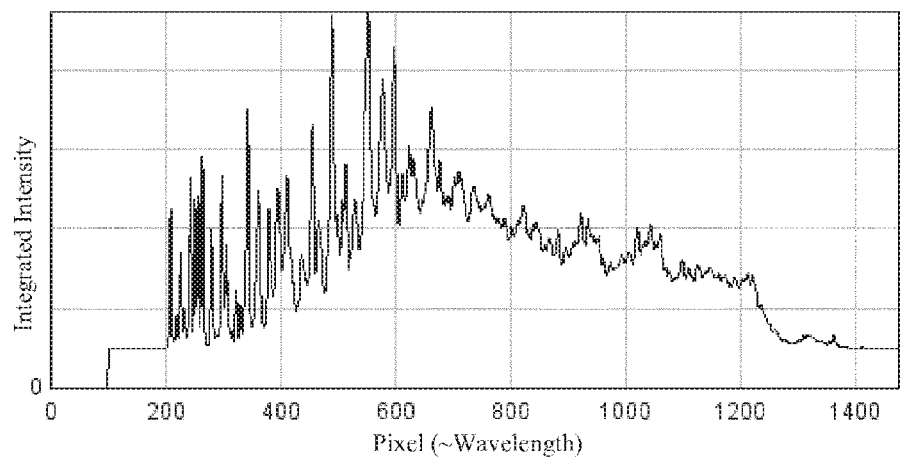
FIG. 4(b)
FIG. 4

Top-down view

Side view

Side view   Spectrometer

Side view

Spectrometer

FIG. 13(b)

INTERFEROMETRY WITH PULSE BROADENED DIODE LASER

PRIORITY

This application is a continuation of U.S. patent application Ser. No. 15/759,486, filed Mar. 12, 2018, which in turn is a National Phase application under 35 U.S.C. § 371 of International Application No. PCT/EP2016/071791, filed Sep. 15, 2016, which claims priority to U.S. Provisional Application Ser. No. 62/219,872, filed Sep. 17, 2015, and U.S. Provisional Application Ser. No. 62/265,107, filed Dec. 9, 2015, all of which are hereby incorporated by reference.

BACKGROUND

High intensity, broad bandwidth light sources are useful for interferometric measurements such as optical coherence domain reflectometry (OCDR), optical coherence tomography (OCT), and self-interference interferometry (SII). High intensity sources are desirable to achieve a large number of constructively interfering photons received back from a weakly reflecting sample that can be Observed on a detector. A continuous, smooth, wide spectrum of optical frequencies is desirable to achieve high spatial resolution in the direction of optical propagation.

OCDR is an interferometric imaging method that determines the scattering profile of a sample along the beam by detecting light reflected from a sample combined with a reference beam. Each scattering profile in the depth direction (z) is called an axial scan, or A-scan. OCT is an extension of OCDR in which cross-sectional images (B-scans), and by extension 3D volumes, are built up from many A-scans, with the OCT beam moved to a set of transverse (x and y) locations on the sample. Modern OCT systems typically collect spectrally resolved data because this allows simultaneous measurement of a range of depths at high depth resolution, without a signal to noise penalty. This method of collecting spectrally resolved data and translating it to a depth resolved measurement via a Fourier transform across the spectral dimension is referred to as "frequency domain" or "Fourier domain" OCT (FD-OCT).

Traditional sources for FD-OCT can be described as producing a broad bandwidth light simultaneously as with superluminescent diodes (SLD) or femtosecond Titanium Sapphire lasers; or as producing a broad bandwidth by sequentially tuning through a range of narrow bandwidths which, when considered together, constitute a broad time integrated bandwidth. The latter type of source may be called a swept source. Examples of swept-sources include external cavity tunable lasers (ECTL), vertical cavity surface emitting lasers (VCSEL), and sampled grating distributed. Bragg reflector lasers (SG-DBR) among others. Simultaneous broad-bandwidth sources are typically detected with a spectrally dispersing element and a linear array of photo-diodes in what is called as spectral domain OCT (SD-OCT). Swept sources are typically detected over time using one or two single element photo-detectors, therefore encoding the spectral information in the time dimension, in what is referred to as swept-source OCT (SS-OCT). Exposure times for SD-OCT systems in the human eye are limited by phase washout (i.e., cancellation of signal during a measurement period due to axial/lateral motion) to about 100 µs. Exposure times for SS-OCT systems are limited to about lens. A hybrid swept source, spectral domain (SS/SD-OCT) arrangement has been described which allowed longer exposure times than a standard SD-OCT system without phase washout (see for example, Yun, S. H., Tearney, G., de Boer, J., & Bouma, B, (2004). Pulsed-source and swept-source spectral-domain optical coherence tomography with reduced motion artifacts. *Optics Express,* 12(23), 5614-5624).

Both SD-OCT and SS-OCT systems have found use in commercial applications, a notable example being the field of ophthalmology. The high brightness simultaneous or swept broad bandwidth sources used in today's commercial ophthalmic OCT systems account for a significant fraction of the total system cost. SS-OCT is a rapidly developing area of OCT; however the cost remains very high, due to which widespread commercial acceptance has not been met yet.

Parallel OCT systems simultaneously illuminate a set of A-scans, whereas traditional point scanning OCT systems illuminate a single lateral point at a time. Field illumination OCT is a subset of parallel OCT where the illumination is contiguous between multiple A-scans (as a line, partial field, or full field) as opposed to spatially separated individual A-scans. Field illumination OCT offers potential benefits in terms of cost relative to point scanning OCT, partly owing to simplifications in fast beam scanning. Parallel OCT systems require similar exposure energy per unit area as traditional point-scanning OCT systems, to achieve similar shot noise limited sensitivity. The constraints on exposure energy and exposure time result in greater source power requirements for parallel systems compared to traditional point-scanning OCT to achieve similar signal-to-noise ratio (SNR) in a single measurement. Some highly parallel SD-OCT systems use two-dimensional (2D) array sensors to measure many points of spectra simultaneously. 2D sensors are commonly available as consumer electronics such as cell phone and security cameras, and can therefore often be found for less than the cost of linear arrays typically found in point scanning SD-OCT systems. The frame rates of these consumer devices are currently typically less than 200 Hz. The short exposure times of SD-OCT, and the slow frame rates of low cost 2D arrays imply a duty cycle less than 2%. This low duty cycle means that an attempt to construct composite scans from serially acquired scans illuminated with a continuous wave (CW) source will have low efficiency (i.e., over time, more than 98% of the power from the source will need to be blocked). Existing superluminescent diodes are moderately expensive and insufficient in terms of power, and existing swept sources are too expensive to power low cost OCT devices that take advantage of the cost benefits of field illumination OCT.

Semiconductor diode lasers can easily achieve single transverse mode power levels on an order of magnitude larger than superluminescent diodes (SLD). When a semiconductor diode material begins to lase, the spectral bandwidth narrows, usually to one or a few very narrow peaks called longitudinal modes which are constrained by the resonance of the laser cavity. Bandwidth as used herein refers to the width of the envelope of the multiple longitudinal modes. Typically, consumer devices such as compact disc readers, laser printers, and rangefinders need the high intensity and spatial coherence provided by a laser, but do not require, or find it disadvantageous to employ a broad bandwidth such as provided by an STD, Although SLD and semiconductor diode lasers largely share the same materials, manufacturing, and packaging techniques, semiconductor diode lasers are often manufactured at low unit costs because of the extremely high volumes utilized in consumer electronics.

Methods of tuning and shaping the spectral output of diode lasers have been developed and employed for various applications including optical coherence tomography and related interference techniques. The temperature dependence of the semiconductor bandgap was one of the first, and most common, methods demonstrated to tune the output of a diode laser, but is usually associated with a response that is too slow and coarse for OCT. A closed loop system has been described in the art where a current controlled thermocouple adjusts the case temperature of the laser package (see for example, Bartl, J., Fíra, R., and Jacko, V. (2002). Tuning of the laser diode. Measurement Science Review volume 2 section 3, hereby incorporated by reference). Rapidly tunable intracavity filters, which precisely restrict the longitudinal mode of the laser, are standard in swept source OCT (see for example, U.S. Pat. No. 5,949,801 hereby incorporated by reference), where it is desirable to smoothly sweep a narrow laser line across a broad bandwidth. The complexity associated with this method results in a high system cost.

The total spectrum from multi-longitudinal mode lasers, which simultaneously produce many closely spaced, narrow bandwidth modes, is relatively broad; however the comb structure on the spectrum causes severe sidelobe artifacts. Such multi-longitudinal mode laser spectra can be blurred over time by forcing the comb spectrum to shift slightly during the measurement period so that the comb peaks move to fill in the spaces in between the peaks. Non-equilibrium thermal effects and carrier density effects can create small changes in refractive index of the laser cavity. These changes in refractive index effectively change the optical length of the laser cavity such that the modes of the cavity shift slightly to blur the comb structure. Wei-Kuo Chen demonstrated the smoothing of a comb spectrum for a depth ranging application by driving a multimode laser with 100 picosecond long pulses which act primarily by changing the optical length of the cavity (by carrier density effects) to shift its resonances (see for example, Wei-Kuo Chen and Pao-Lo Liu, "Short-coherence-length and high-coupling-efficiency pulsed diode laser for fiber-optic sensors," Opt. Lett. 13, 628-630 (1988), hereby incorporated by reference). Such short pulses are difficult to achieve because of the impedance of the drive electronics and the packaging of the diode laser itself.

An interferometric imaging system closely related to OCT was demonstrated using a multimode diode laser and applying a sinusoidal 100 Hz modulation between lasing threshold and approximately max sustainable CW current (see for example, Balboa, I., Ford, H. D., and Tatam, R. P. (2006). Low-coherence optical fibre speckle interferometry. Measurement Science and Technology 17, 605, hereby incorporated by reference). At this much slower modulation frequency, thermal effects are believed to dominate over carrier density effects. The comb structure is blurred to become more ideally Gaussian (therefore suppressing sidelobes), and is broadened by a very modest fraction of 1.2 from 3.2 nm to 4.0 nm ultimately delivering a relatively coarse axial resolution of 165 µm.

In light of the limitations of the current state of the art, there is a need for low cost sources and detector arrangements for use in interferometric imaging systems.

SUMMARY

The present application describes a source, with possible applicability, in one instance, to hybrid SS/SD-OCT, which achieves much greater power than today's SLDs and can be constructed from currently available consumer electronics at much lower cost. The source, among other applications, is particularly well suited to the low duty cycle illumination appropriate for field illumination OCT implemented with consumer grade 2D array sensors with moderate to low frame rates. In one embodiment, a single transverse mode semiconductor diode laser is operated under non-traditional conditions for use in a low-coherence interferometric system. The optical wavelength output of the diode laser is swept over a range greater than 20 nm by applying pulses of drive current, provided by a driver circuit, to the gain medium of the diode laser. The shape of the pulse is optimized to drive the gain medium to vary the output wavelength of the laser over a spectral bandwidth that is at least two times larger than the spectral output bandwidth under equilibrium conditions. In some instances, the spectral output bandwidth is at least five times larger than the spectral output bandwidth at equilibrium. The source may be realized using a low cost diode laser such as one that is commonly used for CD-R optical disk writing, which is optimized for single transverse mode operation and pulsed current >500 mA for pulses between 100 ns and 10 ms and output wavelength at approximately 780 nm. Other semiconductor diode lasers are also equally applicable for this application and may have benefits which outweigh an increased price. For instance, one semiconductor diode laser may have a longer lasing cavity resulting in a tighter spectral comb spacing and thus a smoother spectrum. The longer lasing cavity has the drawback of requiring a higher pulse energy or accepting a narrower overall bandwidth.

The wavelength swept source can be combined with a multiple point imaging spectrometer for a hybrid SS/SD-OCT field sensing system for generating depth information of a sample. Optics illuminate a region of a sample with the beam of radiation provided by the diode laser. Interference signal of the beam returning from the sample (possibly with a reference beam) is detected by the detector, which in one embodiment could be a multiple point imaging spectrometer, and the observed interference over the wide spectral range is converted into depth information of the sample. This arrangement compensates for some non-ideal behavior of the source, and provides a data sampling solution that is well suited to the duty cycle requirements of the source. Minimum phase washout over a long integration time can be achieved by driving a single current ramp over the exposure time of the spectrally resolved detector. Typically the readout rate of the camera is the speed limiting factor in SD-OCT.

Alternatively, phase washout may be enhanced to act more like a traditional SD-OCT exposure by repeated sweeps across the spectrum within the exposure window of the camera. This may be advantageous for example to attenuate signal inside or below blood vessels, which may increase contrast. This may also be useful to suppress signal below the retinal pigment epithelium (RPE) of the eye. In one embodiment, a rolling shutter is described in combination with the hybrid SS/SD-OCT system, where the exposure window is timed to correspond to the potentially exposed region of the sensor during the sweep.

The source and spectrometer design of the present application are particularly well suited for line-field hybrid SS/SD-OCT, sparsely sampled array OCT implemented on a 2D array, and line field self-interference interferometry using a spectrometer.

BRIEF DESCRIPTION OF DRAWINGS

FIG. 1 is a basic schematic of a generalized optical coherence tomography (OCT) system.

FIG. 2 shows operating characteristics of an exemplary prior-art diode laser. In particular, FIG. 2(a) shows a plot of the output power vs. current of the diode laser. FIG. 2(b) shows a plot of the wavelength vs. temperature of the diode laser.

FIG. 3 shows an exemplary pulse ramp increasing from 0 A to 1 A of current over a period of 10 ms, FIG. 4(a) shows the output of a diode laser operating under a drive current pulse that is suitable for interferometric imaging using a 27 kHz linear array spectrometer. FIG. 4(b) shows a time integrated spectrum based on the output shown in FIG. 4(a).

FIG. 13(b) shows a side view of an alternative compact spectrometer design.

DETAILED DESCRIPTION

Figure 5A:
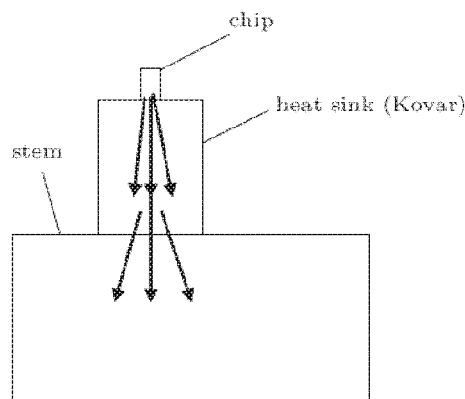
FIG. 5(a) shows an example distribution of heat flux without an AlN submount for a GaN laser diode in a TO 56 package.

All patent and non-patent references cited within this specification are herein incorporated by reference in their entirety to the same extent as if the disclosure of each individual patent and non-patient reference was specifically and individually indicated to be incorporated by reference in its entirely.

Definitions

The following definitions ma be useful in understanding the detailed description:

Interferometric system: A system in which electromagnetic waves are superimposed in order to extract information about the waves. Typically a single beam of at least partially coherent light is split and directed into different paths. These paths are commonly called sample path and reference path, containing sample light and reference light. The difference in optical path length between the two paths creates a phase difference between them, which results in constructive or destructive interference. The interference pattern can be further analyzed and processed to extract additional information. There are special cases of interferometric systems, e.g. common path interferometers, in which the sample light and reference light travel along a shared path.

Optical Coherence Tomography (OCT) System: An interferometric imaging system that determines the scattering profile of a sample along the OCT beam by detecting the interference of light reflected from a sample and a reference beam creating a depth resolved (e.g., 2D/three-dimensional (3D)) representation of the sample. Each scattering profile in the depth direction (z) is reconstructed individually into an axial scan, or A-scan. Cross-sectional images (B-scans), and by extension 3D volumes, are built up from many A-scans, with the OCT beam moved to a set of transverse (x and y) locations on the sample. The axial resolution of an OCT system is inversely proportional to the spectral bandwidth of the employed light source. The lateral resolution is defined by the numerical aperture of the illumination and detection optics and decreases when moving away from the focal plane. OCT systems exist in time domain and frequency domain implementations, with the time domain implementation based on low coherence interferometry (LCI) and the frequency domain implementation based on diffraction tomography. OCT systems can be point-scanning, multi-beam or field systems.

Self-Interference Interferometry (SII) System: An interferometric depth ranging system that reports the distribution of scatters in the object in terms of the product of their reflectivities, and the distance between them. For instance, if the object contains a dominant scatterer on one side of the scattering object, the output is functionally similar to OCT. Each scattering profile in the depth direction (z) is reconstructed individually into an axial scan, or A-scan. Cross-sectional images (B-scans), and by extension 3D volumes, are built up from many A-scans, with the SII beam moved to a set of transverse (x and y) locations on the sample. The axial resolution of an SII system is inversely proportional to the spectral bandwidth of the employed light source. The lateral resolution is defined by the numerical aperture of the illumination and detection optics and decreases when moving away from the focal plane. SII systems exist in frequency domain implementations. SII systems can be point-scanning, multi-beam or field systems.

Optical Coherence Domain Reflectometry (OCDR) System: A term referring to the coherent detection of the location and strength of a scatterer along a beam path, especially for the measuring of fiber lengths. When the technique was extended to include 2D biological imaging, by scanning the beam across a target and assembling the linear profiles into an image, it was commonly referred to as OCT; however, some academic groups retain the original nomenclature for both the non-imaging technique and its derivative imaging technique.

Field illumination system: An interferometric imaging system wherein the sample is illuminated with a contiguous field of light which is then detected with a spatially-resolved detector. This is in contrast to imaging systems which use a focused spot or multiple spatially-separated focused spots with a single detector for each spot. Examples of field illumination systems include line-field, partial-field and full-field systems.

Point-scanning system: A confocal scanning system that transversely scans the sample with a small spot and detects the backscattered light from the spot at a single point. The single point of detection may be spectrally dispersed or split into two channels for balanced detection. Many points have to be acquired in order to capture a 2D image or 3D volume. Cirrus™ HD-OCT (Carl Zeiss Meditec, Inc. Dublin, Calif.) as well as all other commercial ophthalmic OCT devices, are currently point-scanning systems.

Parallel system: An interferometric imaging system that acquires multiple A-scans simultaneously at different positions across a field. The multiple A-scans might be directly adjacent in the case of field illumination, or may sparsely sample a field with distinctly separated points which would need to be serially scanned in order to capture an approximately continuous volume.

Line-field system: A field illumination system that illuminates the sample with a line and detects backscattered light with a spatially resolved detector, Such systems typically allow capturing a B-scan without transverse scanning. In order to acquire an en face image or volume of the sample, the line has to be scanned across the sample in one transverse direction.

Partial-field system: A field illumination system that illuminates an area of the sample which is smaller than the desired field of view and detects the backscattered light with a spatially resolved detector. In order to acquire an enface image or volume of the entire desired field of view one requires transverse scanning in two dimensions. A partial field illumination could be, for example, a spot created by a low NA beam, a line, or any two-dimensional area including hut not limited to a broad-line, an elliptical, square or rectangular illumination.

Full field system: A field illumination system that illuminates the entire desired field of view (FOV) of the sample at once and detects the backscattered light with a spatially resolved detector. In order to acquire an enface image or volume, no transverse scanning is required.

Sparsely sampled array system: A highly parallel system in which many points over a wide field are sampled simultaneously. Distinct sampling points are sparsely distributed across the field (in contrast to contiguous field illumination).

Photosensitive element: An element that converts electromagnetic radiation (i.e. photons) into an electrical signal. It could be a photodiode, phototransistor, photoresistor, avalanche photodiode, nano-injection detector, or any other element that can translate electromagnetic radiation into an electrical signal. The photosensitive element could contain, on the same substrate or in close proximity, additional circuitry, including but not limited to transistors, resistors, capacitors, amplifiers, analog to digital converters, etc. When a photosensitive element is part of a detector, it is also commonly referred to as pixel, sensel or photosite. A detector or camera can have an array of photosensitive elements.

Detector: We distinguish between zero-dimensional (0D), one-dimensional (1D), and two-dimensional (2D) detectors. A 0D detector would typically use a single photosensitive element to transform photon energy into an electrical signal. Spatially resolved detectors, in contrast to 0D detectors, are capable of inherently generating two or more spatial sampling points. 1D and 2D detectors are spatially resolved detectors. A 1D detector would typically use a linear array of photosensitive elements to transform photon energy into electrical signals, A 2D detector would typically use a 2D array of photosensitive elements to transform photon energy into electrical signals. The photosensitive elements in the 2D detector may be arranged in a rectangular grid, square grid, hexagonal grid, circular grid, or any other arbitrary spatially resolved arrangement. In these arrangements the photosensitive elements may be evenly spaced or may have arbitrary distances in between individual photosensitive elements. The 2D detector could also be a set of 0D or 1D detectors optically coupled to a 2D set of detection locations. Likewise a 1D detector could also be a set of 0D detectors or a 1D detector optically coupled to a 2D grid of detection locations. These detection locations could be arranged similarly to the 2D detector arrangements described above. A detector can consist of several photosensitive elements on a common substrate or consist of several separate photosensitive elements. Detectors may further contain amplifiers, filters, analog to digital converters (ADCs), processing units or other analog or digital electronic elements on the same substrate as the photosensitive elements, as part of a read out integrated circuit (ROIC), or on a separate board (e.g. a printed circuit board (PCB)) in proximity to the photosensitive elements. A detector which includes such electronics in proximity to the photosensitive elements is in some instances called "camera."

Spectrometer: A device for measuring light in a spectrally resolved manner. Typically light is separated in angle according to wavelength by a diffractive or dispersive element and focused onto a spatially resolved detector, such that position on the detector encodes optical wavelength. Other types of spectrometers which split the light by other means such as array waveguides, or even computationally such as with Fourier Transform Spectrometers, exist. Spectrometers may measure a single beam path or multiple beam paths. A spectrometer that simultaneously resolves multiple beam paths is frequently termed an imaging spectrometer.

Light beam: Should be interpreted as any carefully directed light path.

Coordinate system: Throughout this application, the X-Y plane is the enface or transverse plane and Z is the dimension of the beam direction.

Drive Current: Electrons that flow across the active junction of a semiconductor laser device to stimulate the release of photons at the energy associated with the bandgap of the active junction.

Current Pulse: A short-term increase in the drive current above a baseline level.

Pulse train: A sequence of current pulses.

Burst: A pulse train consisting of a small number of pulses in rapid succession

Speckle diameter: A region over which an observation of interference has highly correlated phase. This measure is highly correlated with the resolution and point spread function of a interferometric imaging system (see for example, Schmitt, J. M., Xiang, S. H., and. Yung, K. M. (1999). Speckle in Optical Coherence Tomography. J. Biomed. Opt 4, 95-105).

General OCT System

A diagram of a generalized ophthalmic OCT system is shown in FIG. 1. A beam of light from source 101 is routed, typically by optical fiber 105, to illuminate the sample 110, a typical sample being tissues in the human eye. The source 101 is typically either a broadband fight source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (in x and y) over the region of the sample to be imaged. Light scattered from the sample is collected, typically into the same fiber 105 used to route the light for sample illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference that is observed using a detector 120. Although a single fiber port is shown going to the detector, those skilled in the art recognize that various designs of interferometers can be used for balanced or unbalanced detection of the interference signal. The output from the detector 120 is supplied to a processor 121 that converts the observed interference into depth information of the sample. The results of the processing can be stored in the processor 121 or other storage medium or displayed on display 122. The processing and storing functions may be localized within the OCT instrument or functions may be performed on one or more external processing units to which the collected data is transferred. This unit could be dedicated to data processing or perform other tasks which are quite general and not dedicated to the OCT device. The processor 121 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, one arm of the interferometer typically contains a tunable optical delay to generate a time variable ramp in the interference phase across the spectrum. Balanced detection systems are typically used in TD-OCT and SS-OCT systems, while spectrometers are used at the detection port for SD-OCT systems.

In Fourier Domain optical coherence tomography (FD-OCT), each measurement is the real-valued spectral interferogram ($S_j(k)$). The real-valued spectral data typically goes through several post-processing steps including background subtraction, dispersion correction, etc. The Fourier transform of the processed interferogram, results in a complex valued OCT signal output $A_j(z)=|A_j|e^{j\varphi}$. The absolute value of this complex OCT signal, $|A_j|$, reveals the profile of scattering intensities at different path lengths, and therefore scattering as a function of depth (z-direction) in the sample. Similarly, the phase, $\varphi_j$ can also be extracted from the complex valued. OCT signal. The profile of scattering as a function of depth is called an axial scan (A-scan). A set of A-scans measured at neighboring locations in the sample produces a cross-sectional image (tomogram or B-scam) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. A variety of ways to create B-scans are known to those skilled in the art, including but not limited to scanning the sample beam along the horizontal or x-direction, along the vertical or y-direction, along the diagonal of x and y, or M a circular or spiral pattern.

Pulse Tuning the Source

In one aspect of the present application, a common semiconductor diode laser is supplied with a drive current such that its spectral output is optimized for interferometry applications such as OCT, OCDR, or SII. An exemplary diode laser for this purpose is LNCT28PF01WW produced by Panasonic, described as an edge emitting, Fabry-Perot, 780 nm band diode laser with multi quantum well structure. The laser is selected for having a wavelength appropriate to a given task, for example ophthalmic imaging of the eye (in this case, a wavelength with good water penetration and low visual excitation potential are desirable). Preferably, the laser should have a significant and approximately continuous dependence of wavelength on operating temperature. The optical path length of the laser cavity (i.e., its physical length multiplied by its refractive index) is preferably long, such that the longitudinal modes are closely spaced. The end facets of the laser are preferably optimized for high peak optical power. Preferably, the laser outputs a single spatial mode so any portion of the sampled beam can be expected to interfere with high contrast with another part of a sampled beam. Finally, the laser is preferably used in a high volume application and therefore is likely to be available at very low cost. The compact disk read-write application offers the combination of compatible wavelength range, high-power, single transverse mode pulses, as well as a very large and price sensitive market.

FIG. 2 shows the published operating characteristics of the diode laser LNCT28PF01WW by Panasonic. FIG. 2(*a*) shows a plot of the output power vs. current while FIG. 2(*b*) shows a plot of the wavelength vs. temperature of the diode laser. The maximum recommended continuous wave (CW) current is about 300 mA. Driving the slightly cooled diode at minimum CW current results in an output wavelength of less than 780 nm, which gives a good indicator of the minimum wavelength practical with this diode. Driving the diode near its maximum CW current at its maximum operating temperature should drive the junction near to its operating temperature limit resulting in a wavelength greater than 800 nm.

The diode laser light source typically has a spectral output bandwidth <1 nm when driven under equilibrium conditions (constant current and temperature). The diode laser is operably attached to a driver circuit capable of applying pulses of drive current to the diode laser. For the embodiments described herein, the drive current pulse is designed to produce an output spectrum of suitable shape for interferometric applications when integrated over time. To achieve such a usable shape output spectrum, certain design considerations should ideally be achieved, some of which are discussed as follows:

1. The pulse of drive current should cause the laser active junction to achieve a significant widening of the laser bandwidth, with the increase in bandwidth being ideally at least as large as the spectral output bandwidth under equilibrium operating conditions as described above (thus doubling the spectral output bandwidth). In some instances, the spectral output bandwidth is at least five times larger than the spectral output bandwidth at equilibrium. Most likely this spectral shift is due to temperature changes. An increase in temperature causes a decrease in the material bandgap resulting in a shift of the peak gain of +0.3 nm/C for GaAs (see for example, Bartl, J., Fíra, R., and Jacko, V. (2002). Tuning of the laser diode. Measurement Science Review volume 2 section 3). Ideally the temperature sweep during a drive current pulse covers a range from a lower baseline temperature to a point near an upper practical operating limit of the laser. The lower baseline temperature may be actively cooled below the ambient temperature to increase the available temperature range. The upper operating limit of the laser may be defined either as a temperature where the laser efficiency is highly reduced, or where running the laser hotter would reduce its lifetime beyond usability for the application.
2. The pulse of drive current should deliver a significant amount of optical energy while operating at each wavelength so as to produce a usable shaped time integrated spectrum. Joule heating most likely causes the temperature of the active junction to rapidly rise to an approximate equilibrium. To first order, this temperature rise can be described by $\Delta T(t)=T_o[1-\exp(-t/\tau)]$, where $\tau$ is a thermal time constant of the diode junction typically on the order of a few hundreds of nanoseconds. The thermal time constant is the time required for junction to reach $1-1/e\sim63.2\%$ of the final change in temperature upon a step increase in current. The output spectrum of the laser may then provide a good estimate of the junction temperature. Frequently an approximately Gaussian shaped spectrum is considered desirable.
3. The pulse of drive current should cause cavity length shifts which change the position of the laser lines enough to blur the line structure in the time integrated spectrum. The cavity length shift is a result of index of refraction changes due to a combination of injection current effects and temperature changes.
4. The pulse duration should be sufficiently short as to avoid any artifacts such as fringe washout as described in the Background section. For a preferred embodiment of a hybrid SS/SD-OCT system, the preferred pulse duration would likely be shorter than 1 ms while for an SD-OCT system, the preferred pulse duration would likely be shorter than 100 µs.
5. The characteristics of the drive current, such as the temporal profile, the peak current, and the repetition rate, should be designed in a way that pulsing the diode laser does not damage it or significantly reduce its lifetime for any practical OCT application. Because of the low cost of the diode laser, several hundred hours of operation are likely possible since users can replace with a new one if it is damaged.

The temporal profile of the current pulse may comprise a polynomial, an exponential function, or any other time-varying shape that could meet the above goals. Likely examples include rectangle or a linear ramp. For instance, a short pulse of approximately constant current, of duration on the order of the thermal time constant of the junction or less, is one such way to achieve a spectrum that is approximately flat (because the temperature vs time curve is approximately linear in this short time period). The equilibrium temperature for the approximately constant current is significantly larger than the final temperature at the end of the linear temperature range. If such a pulse achieves a large change in temperature, the equilibrium temperature may be very high, potentially beyond the temperature required to destroy the diode, such as by melting the solder layers. Therefore, the diode is operated in a regime where the peak junction temperature is critically dependent on the duration of the pulse, which should be less than a few hundreds of nanoseconds, depending on the structure of the diode.

The rectangular pulse described above has relatively small energy because the pulse duration is very short. In order to increase the amount of energy, a pulse train consisting of many short pulses can be constructed. Such short, critically timed pulses may be created with small modification to circuitry used to drive compact disk write cycles, which typically deliver high current pulses for durations on the order of 500 ns or shorter.

An alternative pulsing regime that also produces a usable shaped time integrated spectrum, drives the current with a slow pulse so that the junction temperature stays very close to the equilibrium temperature associated with the drive current at all times. The pulse may preferably be shaped to produce a desired time integrated spectrum. Because, 1) the optical output power is approximately proportional to current, 2) the heating is approximately proportional to the current squared, and 3) the temperature change is approximately proportional to the heating, a desirable shape for the current ramp tends to have an increasing slope at high currents. The shape of the current ramp can be further controlled to shape the time integrated spectral energy envelope to a desired form such as flat top, Gaussian or Hamming, for the purposes of achieving a desired axial point spread function with minimum noise and post process modification.

FIG. 3 shows an exemplary pulse ramp increasing from 0 A to 1 A of current over a period of 10 ms. This current ramp is sufficient to cause the LNCT28PF01WW diode laser (described earlier with respect to FIG. 2) to sweep over an optical bandwidth of more than 20 nm. Such a low electrical bandwidth pulse is easy to generate with a low cost current driver modulated by input voltage. The input current ramp may be created by analog or digital waveform synthesis such as simple resistor-capacitor circuits in combination with TTL chips such as a simple 555-timer.

FIG. 4(a) shows the output of a diode laser under a drive current pulse suitable for interferometric imaging using a 27 kHz linear array spectrometer to resolve the swept spectrum vs time. Time increases from top to bottom in the figure. Individual longitudinal modes form short bright line segments across the time vs wavelength space. A nearly vertical Line (401) indicates that a resonant mode has a nearly constant wavelength. A line with significant horizontal tilt (402) indicates that the resonance is shifting because of index of refraction changes which cause a slight shill in the apparent length of the laser cavity. Up to several longitudinal modes of the laser may be simultaneously illuminated at a given drive current (405). The illuminated modes sweep toward longer wavelengths (right) as the laser junction heats up under increased drive current (bottom). The total swept bandwidth (406) is much greater than the bandwidth at any fixed current. The exposure time associated with any particular wavelength (407) is much shorter than the total exposure time (408).

FIG. 4(b) shows the time integrated spectrum from the experimental data shown in FIG. 4(a). The horizontal axis is displayed in pixel number which is proportional to wavelength, Pixel 200 is approximately 785 nm. Pixel 1300 is approximately 810 nm. At shorter wavelengths associated with very low current, line spectra associated with unblurred modes are highly visible. At longer wavelength associated with greater current, distinct modes have blurred to fill in the complete spectrum.

Figure 5B:
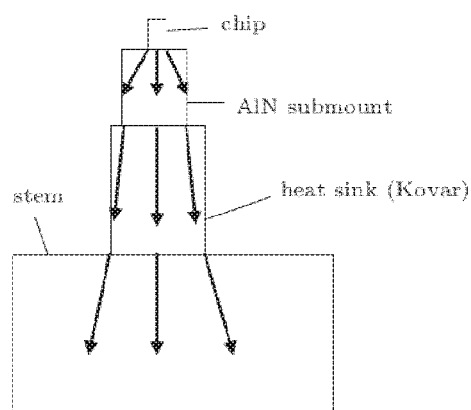
FIG. 5(b) shows the distribution of heat flux with the AlN submount.

In typical interferometric imaging systems like OCT, OCDR and SII, it is desirable to acquire repeated measurements. Therefore, we consider not only the characteristics of a single pulse, but also a sequence of pulses used to operate the device. During the pulse, heat is generated, which must eventually be dissipated to the environment, but is first distributed to the elements of the diode package, typically including: the rest of the semiconductor chip, electrical solders and connections, and submounts. FIG. 5(a) shows the distribution of heat flux without an aluminum nitride (AlN) submount for a GaN laser diode in a TO 56 package (see for example, Feng, M.-X., Zhang, S.-M., Jiang, D.-S., Liu, J.-P., Wang, H., Zeng, C., Li, Z.-C., Wang, H.-B., Wang, F., and Yang, H. (2012). Thermal analysis of GaN laser diodes in a package structure. Chinese Physics B 21, 084209). FIG. 5(b) shows the distribution of heat flux with the AlN submount. The temperature of the active junction (e.g., at the bottom surface of the chip) will generally not reduce below the temperature of the bulk material which is limited by the average current. To reach high temperatures, it is desirable to have a high peak current; on the other hand, to drive the junction over a wide range of temperatures, the junction should have a low baseline temperature to start at, or return to, therefore, the average current would ideally be kept low. This implies delivering pulses with a tow effective duty cycle. The baseline temperature to which the junction returns to will be limited by the average current during a time corresponding to a characteristic time of the device. Operation of many pulses with high duty cycle will result in an upward creeping temperature, shift towards longer wavelength, and decreasing efficiency of the diode laser.

Figure 6A:
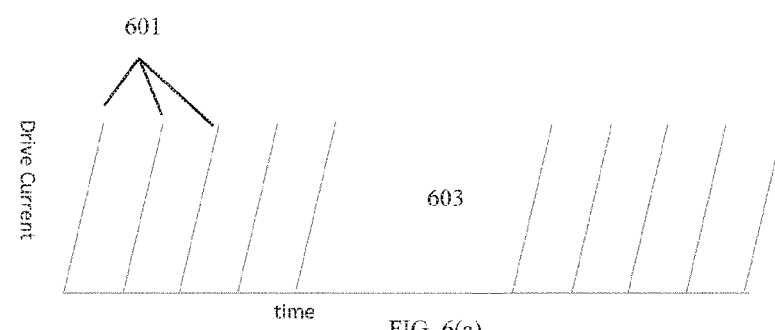
FIG. 6(a) illustrates a drive current vs. time chart when multiple pulses of drive current are delivered in a sequence.
Figure 6B:
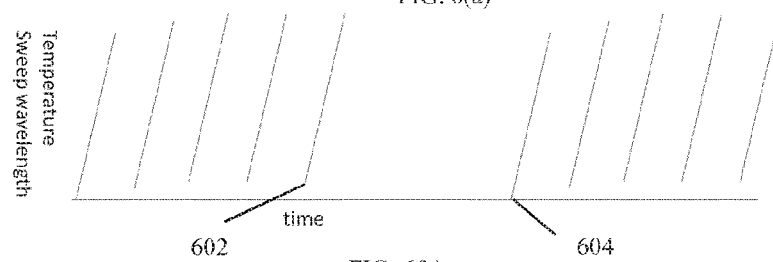
FIG. 6(b) illustrates the resulting time dependent junction temperature.

FIG. 6(a) illustrates a drive current vs, time chart when multiple pulses of drive current (601) are delivered in a sequence. The resulting time dependent junction temperature is illustrated on the lower chart in FIG. 6(b). On multiple pulses in sequence, the minimum temperature (602) drifts toward a temperature associated with the mean drive current in the pulse train. A long recovery period (603) between bursts allows the temperature to return to a lower baseline (604). Increasing time between bursts or pulses can decrease the baseline temperature and allow a total greater bandwidth sweep.

Understanding the thermal characteristics of the diode laser will help design optimal drive current pulse trains to achieve optimal bandwidth and duty cycle. Each element of the package can be characterized by its thermal resistivity and thickness. These characteristics describe the time required for heat to move from a warmer area to a cooler area. In general, one can think of the temperature of parts of the package which are close to the active area as responding very rapidly to the instantaneous current, whereas parts which are farther away respond more slowly and appear to follow the average current, Frequently the package design is such that the largest resistance to heat flow is relatively distant from the active junction. If the pulses are long relative to the thermal equilibrium time of the active junction, the temperature of the diode is well controlled, without tight requirements on the timing precision of the pulse. If the pulses are short relative to the thermal equilibrium time of larger parts of the diode package, the small parts can cool rapidly because the heat has not significantly raised the temperature of the bulk heatsink.

Figure 7A:
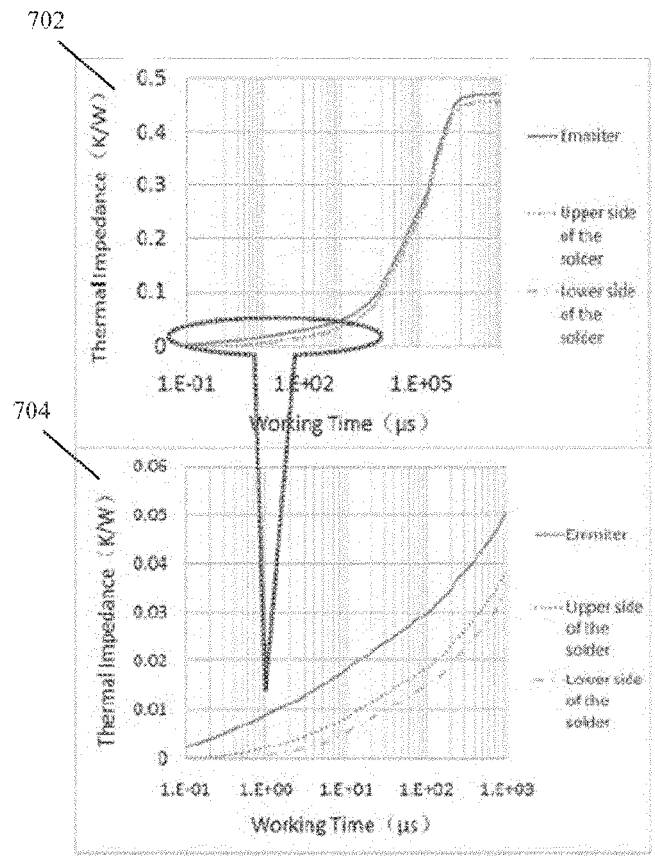
FIG. 7(a) is a plot of thermal impedance vs. time for a high power diode laser.
Figure 7B:
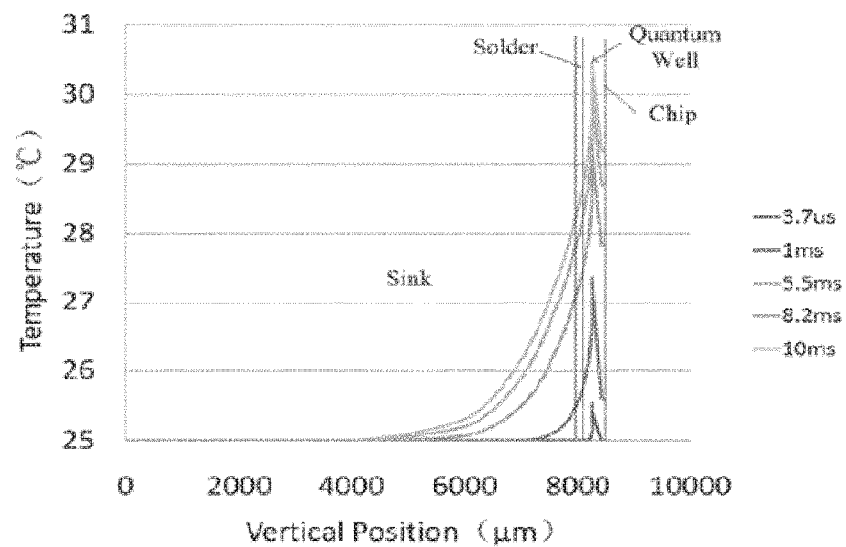
FIG. 7(b) shows the vertical temperature profiles of a single emitter during various heating times.

FIG. 7(a) is a plot of thermal impedance vs. time for a high power diode laser without voids in the solder layer (see for example, Suhir, E., Wang, J., Yuan, Z., Chen, X., and Liu, X. (2009). Modeling of thermal phenomena in a high power diode laser package. In Electronic Packaging Technology & High Density Packaging, 2009. ICEPT-HDP'09. International Conference on, (IEEE), pp. 438-442). The bottom panel 704 in FIG. 7(a) is a zoomed in view of the data in the top panel 702, FIG. 7(b) shows the vertical temperature profiles of a single emitter during various heating times. The figures show that heat flows easily from the junction for short pulses, but becomes more difficult as the package becomes warmer from a history of usage. That is, the laser wilt cool rapidly and nearly completely from a single short pulse, but recovery from a long pulse train will take more time.

The spectral bandwidth sweep achievable with the present technique is typically less than 30 nm, which is somewhat less than the spectral bandwidth achieved by modern SLDs. The range may be extended by cooling of the package below room temperature or by combining multiple diodes with neighboring spectral ranges.

Use of Pulse Tuned Source in a Double-Pass Interferometric System

Figure 8:
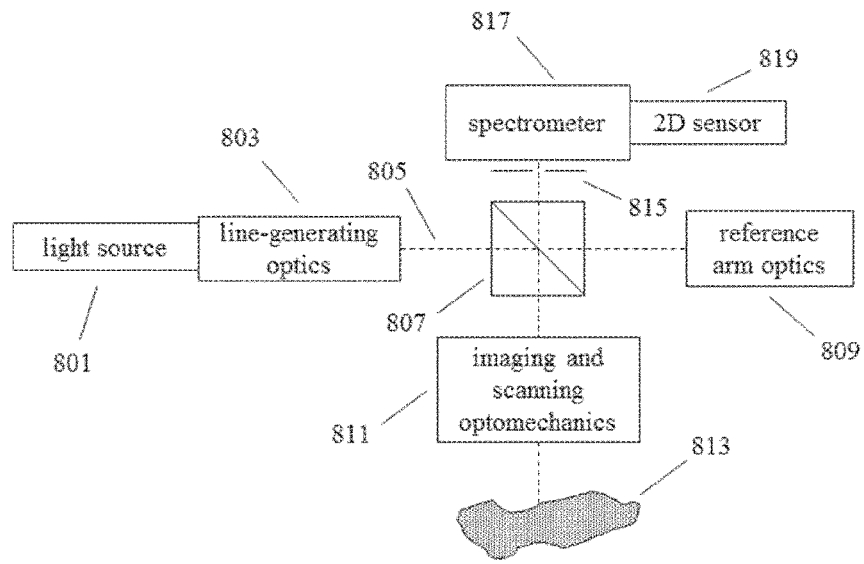
FIG. 8 illustrates an exemplary line field hybrid SS/SD-OCT system embodying a semiconductor diode laser light source discussed in the present application.

The swept diode laser source described in the previous section is optimally integrated into a depth ranging system which makes good use of its potentially high output power, swept wavelength characteristics, and is compatible with its low duty cycle. A first preferred embodiment is configured as a line field hybrid SS/SD-OCT system as illustrated in FIG. 8. The hybrid configuration accommodates the non-ideal instantaneous linewidth of the source, which has been observed to be far from ideally narrow at portions of the sweep, while the swept nature of the source allows for a long exposure time for maximum signal. The semiconductor diode laser (801) light is spread by asymmetric optics (803) such as cylinder or Powell lenses to create a line of illumination. The light beam (805) is split by a beamsplitter (807) and one path becomes a reference path which is reflected by use of optical components (809). Depending on the application, the optics in 809 may also contain asymmetric optics such as a cylindrical or Powell lens. The other path from the beamsplitter is directed to a sample (813) through optics and an optional scanning mechanical component (811). As a line-field system provides a single B-scan for each exposure of the camera, it may not be required or even desired to provide volumetric scanning through a scanner. Such systems would further decrease the overall cost and physical footprint. Light from the illuminated sample is imaged onto the optional entrance slit (815) of a spectrometer (817). Light from a reference arm simultaneously illuminates the optional entrance slit of the spectrometer 817, and interferes with the light from the sample 813. The spectrometer 817 disperses the light transmitted through the slit 815 by wavelength onto a 2D area detector (camera) (819). The modest frame rate of the low cost 2D array provides a good effective A-scan rate, while being compatible with the low duty cycle of the source. A processor (such as the processor 121 (see FIG. 1)) converts the recorded spectrum into B-scan data, which may be further be processed to produce depth maps etc. and displayed on a display (e.g., the display 122 in FIG. 1)

Because of the potential for high power, the desirability of low duty cycle, the instantaneous spectral characteristics, and the cost of this source; it is particularly well suited to highly parallel spectral domain implementations with a 2D array detector. Line-field approaches enabled by this source are particularly well suited to performance requirements of minimum cost applications including slit-lamp based OCT and self-interference OCT. Sparsely sampled array OCT as described by Anderson et al. (see for example, Anderson, T., Segref A., Frisken, G., & Frisken, S. (2015, March). 3D spectral imaging system for anterior chamber metrology. In *SPIE BiOS* (pp. 93120N-93120N), international Society for Optics and Photonics) is also well suited to this source. Although not all of the synergies noted for the above configurations may be present, the source may also be used as a low cost source for point-scanning SD-OCT (see for example, Yun, S. H., Tearney, G., de Boer, & Bouma, B. (2004). Pulsed-source and swept-source spectral-domain optical coherence tomography with reduced motion artifacts. *Optics Express*, 12(23), 5614-5624), point scanning parallel SD-OCT (see for example, Anderson, T., Segref, A., Frisker, G., & Frisken, S. (2015, March). 3D spectral imaging system for anterior chamber metrology. In *SPIE BIOS* (pp. 93120N-93120N). International Society for Optics and Photonics), line-field SS-OCT (see for example, Grajciar B., Pircher M., Fercher A., and Leitgeb R. (2005). Parallel Fourier domain optical coherence tomography for in vivo measurement of the human eye. Optics Express 13, 1131-1137; Nakamura, Y., Makita, S., Yamanari, M., Itch, M., Yatagai, T., & Yasuno, Y. (2007). High-speed three-dimensional human retinal imaging by line-field spectral domain optical coherence tomography. *Optics express*, 15(12), 7103-7116; and Fechtig, D. J., Grajciar, B., Schmoll, T., Blatter, C., Werkmeister, R. M., Drexler, W., & Leitgeb, R. A. (2015). Line-field parallel swept source MHz OCT for structural and functional retinal imaging. *Biomedical optics express*, 6(13), 716-735), full field SS-OCT (see for example, Bonin, T., Franke, G., Hagen-Eggert, M., Koch, P., & Hüttmann, G. (2010), In vivo Fourier-domain full-field OCT of the human retina with 1.5 million A-lines/s. *Optics letters*, 35(20), 3432-3434.), Fall field TD-OCT (see for example, Watanabe, Y., Hayasaka, Y., Sato, M., & Tanno, N. (2005). Full-field optical coherence tomography by achromatic phase shifting with a rotating polarizer. *Applied optics*, 44(8), 1387-1392), low-coherence holography (see for example, Girshovitz, P., and Shaked, N. T. (2014). Doubling the field of view in off-axis low-coherence interferometric imaging. Light Sci Appl 3, e151), or any other interference technique where it is advantageous to use a low cost, high power, source with significant bandwidth.

The source is pulsed to produce a single sweep of a duration corresponding to approximately the maximum time where motion artifacts are rare or manageable. For the human eye this pulse length with a swept source is a little longer than lens (see for example, Fechtig, D. J., Grajciar, B., Schmoll, T., Blatter, C., Werkmeister, R. M., Drexler, W., Leitgeb, R. A. (2015). Line-field parallel swept source MHz OCT for structural and functional retinal imaging. *Biomedical optics express*, 6(3), 716-735). For a hybrid SS/SD-OCT system, we would expect the preferred pulse duration to thus be less than 1 ms. For most samples, the ratio of this pulse length to the frame period of the camera (limited to about 100 Hz in most low cost 2D arrays used in consumer cameras) provides a duty cycle of a few percent which is highly compatible with maintaining a wide bandwidth thermal sweep. The reference arm may be incident on axis or off axis (see for example, US Patent Publication No. 2014/0028974) depending on the desired spectrometer and sensor resolution tradeoff. Spectral resolution provided by the grating spectrometer can be superior to the spectral resolution which would be attained by using the source as a time resolved swept source, because the source frequently supports multiple longitudinal modes with a significant instantaneous bandwidth. Calibration of the spectrometer is also straightforward, whereas calibration of the sweeping source may be quite complex as the tuning curve is not strictly monotonic.

Duration of Laser Pulse and Camera Exposure

The pulse may also be optimized to produce an optimal interference measurement. To maximize signal intensity, it is desirable to maximize the number of photons returned from the sample with a constant interference phase. In measurements of living systems, motion of the sample typically limits the amount of time in which an observation can have a constant interference phase. Axial motion of the sample by a distance of one quarter of a wavelength of light relative to a reference causes a phase difference of 180 degrees, completely reversing the nature of interference, and potentially eliminating signal during the measurement period.

In addition, lateral motion by a significant fraction of the speckle diameter causes a decorrelation of the phase between the beginning of the measurement period and the end of the measurement period with similar loss of signal results. Such cancellation of signal during a measurement period is called phase washout. In measurement systems with a low numerical aperture, such as the human eye, the speckle diameter is much larger than the wavelength of light. As a result, motion in the axial direction is typically the more limiting case. It is typically desirable to take OCT measurements fast enough to avoid washout, although other cases do exist (e.g. optical lock-in). Axial phase washout is determined by the amount of motion experienced during the exposure time associated with any single wavelength. In the case where we wish to minimize phase washout, it is best to drive the laser to achieve a single sweep of wavelength across the measurement integration time period. In this way, each wavelength sample is measured for a small fraction of the total sweep time. In the case where we want to maximize the phase washout, we may drive the laser through many sweeps during a single integration period. In this way, each wavelength is sampled at multiple time points over a relatively long measurement time. Ideally a large number of sweeps is included such that the signals are likely to cancel completely if there is significant motion. Similarly, if the source is used in time domain applications, the pulse modulation rate should be fast compared to the phase modulation between the sample and reference arms.

Figure 9:
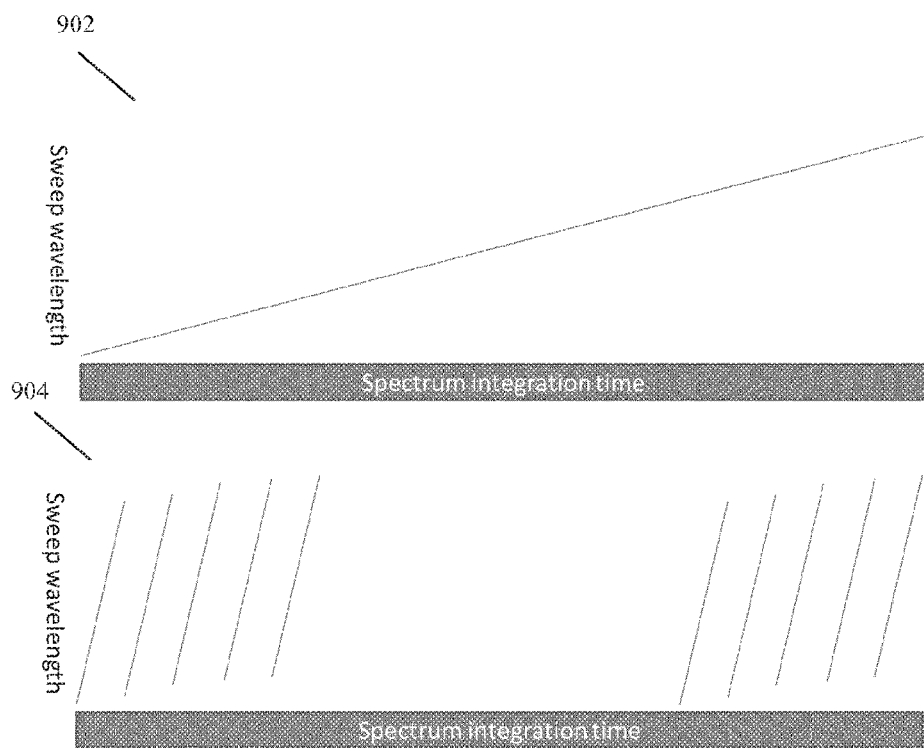
FIG. 9 shows plots of the sweep wavelength vs. the spectrum integration time for two example scenarios.

FIG. 9. shows plots (902) and (904) of the sweep wavelength vs. the spectrum integration time for two different scenarios. In the normal case such as the one depicted in plot (902), phase washout is minimized by actuating a single wavelength sweep over an integration period. In rare cases such as the one depicted in plot (904), where it is advantageous to introduce phase washout, the wavelength may be swept multiple times during a single integration period.

Many consumer grade CMOS 2D sensor arrays are operated in what is known as rolling shutter mode. A timing schematic of this operation is depicted in FIG. 10(*a*). In rolling shutter mode, the entirety of each frame in the capture sequence is not exposed from exactly the same start and end time, but the integration start and end is rastered across the surface of the detector. Rolling shutter mode is advantageous in the hybrid swept-source, spectral domain system described herein to synchronize the exposure window of the camera with the portion of the array that is being instantaneously illuminated by the swept source. The orientation and timing of the rolling shutter can be optimized to best match the illumination of the sensor as it traverses across the surface of the sensor according to its wavelength sweep and the dispersion of the spectrometer. Preferably, the read out raster direction is oriented such that elements of the same wavelength are read out as close to simultaneously as possible. Also preferably, the read out raster direction is oriented such that the wavelengths that are produced first in a sweep of the laser arc read out first. That is, the direction of the rolling shutter is in the same direction as the sweeping of the light across the detector. And preferably, the shutter is opened on a region of the detector shortly before that region of the detector is illuminated by the wavelength sweep, and is closed shortly after that region of the detector is illuminated by the wavelength sweep, thereby minimizing the detector dark current by keeping the integration time short compared to the frame rate of the camera and the duration of the laser sweep. An integration time that is windowed closely to the wavelength sweep of the laser also limits the effect of stray light in the spectrometer. The width of the integration time should be wide enough to allow for the maximum instantaneous spectral width of the source, as well as to accommodate tolerance for sweep rate non-linearities, timing uncertainties, and projection distortions across the detector, There may also be a pause between two sweeps to allow for the diode laser to recover if necessary. Two diode lasers could also be interleaved to allow one to rest on odd sweeps and the other to rest on even sweeps.

Figure 10A:
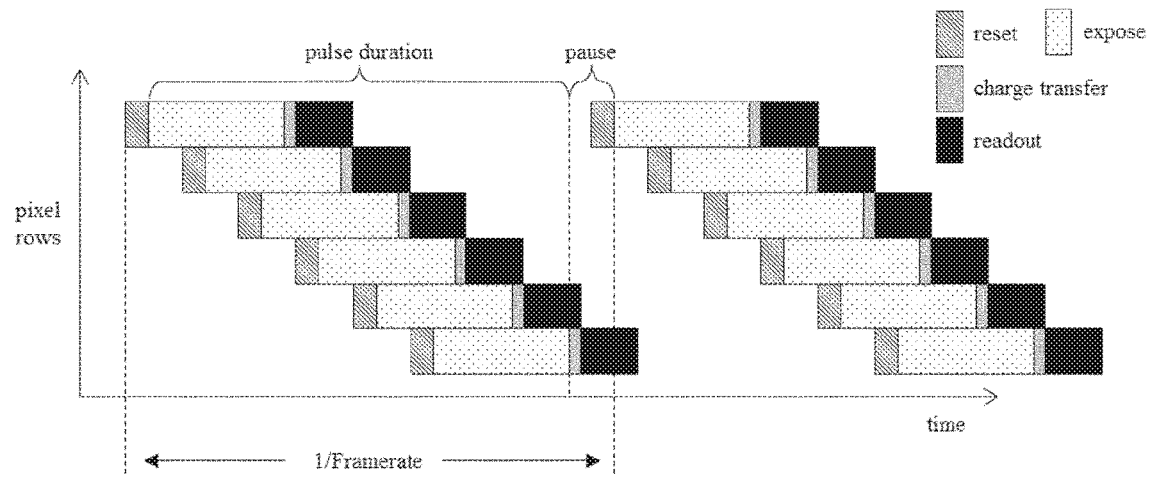
FIG. 10(a) illustrates a timing schematic of consumer grade CMOS 2D sensor arrays operating in a rolling shutter mode.

During a rolling shutter exposure (FIG. 10(a)), the exposure of multiple rows are overlapped and thus it is not necessary for the sweep speed to exactly match the rolling shutter speed. In cases where the readout rate is limited by the sensor array, and the source sweep time is very short compared to the maximum readout period of the sensor, a small reduction in the shutter open time can be achieved by preferably orienting the readout direction relative to the wavelength sweep direction as described above. In this case, the laser sweep should be initiated with a delay after the open shutter signal begins to cross the detector, such that the sweep will finish just as it catches up with the open shutter signal. The close shutter/readout signal may begin approximately simultaneously with the beginning of the wavelength sweep of the source and will continuously lag behind the sweeping light source due to its slower rate across the sensor.

Figure 10B:
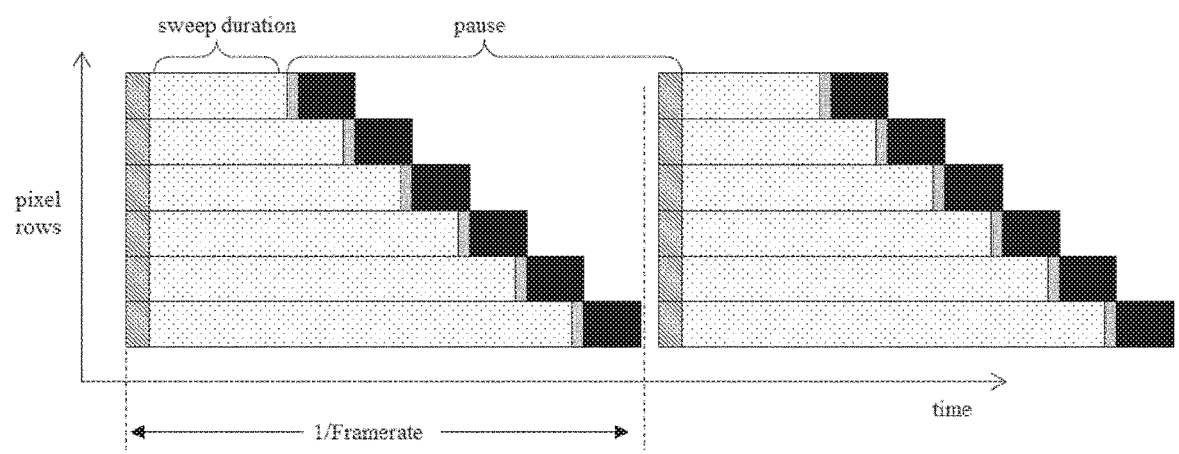
FIG. 10(b) illustrates a timing schematic of this operation in a 'half-global shutter' mode.

Another suitable configuration of the camera is what is called 'half-global shutter' mode and a timing schematic of this operation is depicted in FIG. 10(b) in this mode, all pixels on the camera are reset and begin exposure simultaneously. During this time, the sample is illuminated which, in our setup refers to one or more sweeps of the semiconductor diode laser.

Once the illumination is completed, each row of pixels is read out one-by-one while the other rows continue to be exposed. This mode of operation exists because the minimal charge-transfer and readout electronics on the camera only allows for one row to be captured and transferred at a time. In contrast to the rolling shutter mode as depicted in FIG. 10(a), this mode allows for very short sweep times with long pauses between pulses. One disadvantage is the increased noise characteristics when compared to a true global shutter or a rolling shutter.

Figure 10C:
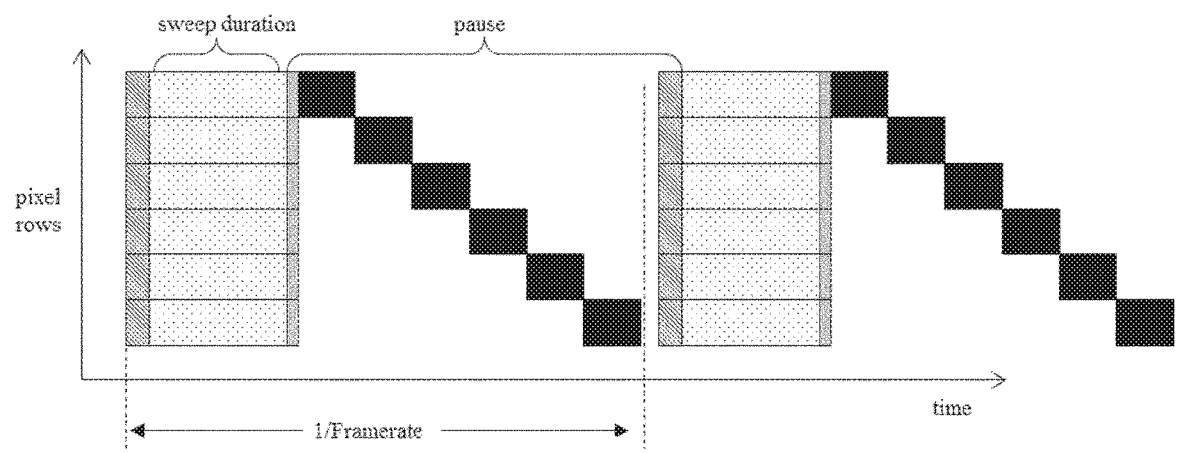
FIG. 10(c) illustrates a timing schematic of this operation in a 'true global shutter' mode.

A timing schematic of a 'true global shutter' mode is depicted in FIG. 10(c). In this mode, all pixels begin and end exposure at the same time. Extra electronics (when compared to rolling shutter or half-global shutter) allow for the charge from each pixel to be transferred and stored temporarily while each row is read out one-by-one. This mode of operation is not commonly found in low-cost 2D sensors.

Image Processing Techniques

When using the semiconductor diode laser source discussed herein in an interferometric system (tar example, with respect to FIG. 8), it is often desirable to perform background subtraction to remove any low-frequency variations introduced by the reference beam. Because of the diode laser ideally being driven under loosely controlled conditions, or under repeated pulses in non-equilibrium conditions, the spectrum shape may vary significantly from cycle to cycle. Parallel detection arrangements provide additional advantages in processing an unstable spectrum.

One possibility is for a detector channel to sample the source spectrum without interference in parallel with the usual interferometric detection. In a line-field hybrid SS/SD-OCT system, for instance, this could be achieved by blocking the sample light from hitting part of the 2D detector. Using this area and knowledge of the varying PSF across the detector, the background spectrum could be accurately estimated across the detector, Another possibility is to use multiple detection channels with interference to estimate the source spectrum on a per sweep basis. If these measurements vary in some way (be it the phase delay, spatial sampling location, spatial sampling angle, etc.), the mean (or some other combination) of some or all of the A-scan channels could be used as an estimate of the spectrum A variety of other estimation approaches are possible which include, but are not limited to, median, maximum-likelihood estimation, and estimation filters (linear or non-linear) such as the Kalman filter.

To improve the shape of the acquired spectrum, the interference spectrum associated with each A-scan can be divided by the estimate of the source spectrum to create a normalized spectrum, and multiplied by a windowing function to optimize spectral shape, therefore optimizing the axial point spread function in the reconstructed image. In some regions of the spectrum where the peaks modulate to large degrees, spectral normalization may be highly susceptible to noise. Thus, it may be beneficial to use the windowing function to partially attenuate these wavelengths which allows for the smoother portions of the spectrum to dominate. The order of these multiplicative steps is generally somewhat mutable and may be combined with other steps including resampling, dispersion compensation, background subtraction, etc. and in some cases may even be applied (as a convolution filter) on the other side of a Fourier transform or filter bank operation.

One computationally expensive step in OCT image processing is resampling the acquired data to be linear-in-k space, Such a step is typically performed using interpolation algorithms such as nearest neighbor, linear, quadratic, cubic, spline, sine, etc. Especially for a low-cost OCT system, minimizing the required computational power is desirable. The less computationally expensive interpolation methods typically provide lower image quality. Somewhat unique to this low-cost OCT system is the small to moderate measured optical bandwidth. As such, the non-linearity in the bandwidth should be small and thus it may be possible to utilize simpler interpolation techniques than for higher-performance systems (perhaps as simple as a nearest-neighbor interpolation), Furthermore, provided with the small optical bandwidth, and the availability of detectors with a large number of pixels (such as 1024 or more pixels), a large imaging depth is easily obtainable, minimizing the possibility of image aliasing during the interpolation step. This can further simplify the interpolation technique.

Use of Pulse Tuned Source with a High-Efficiency Interferometer

Figure 11A:
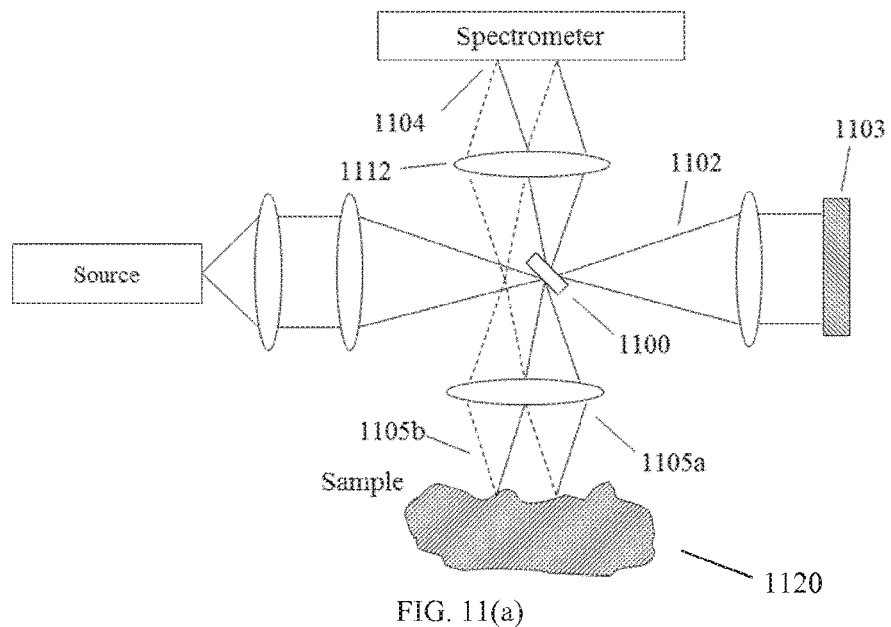
FIG. 11(a) is a top-down view of a high-efficiency interferometer embodying a semiconductor diode laser light source discussed in the present application.
Figure 11B:
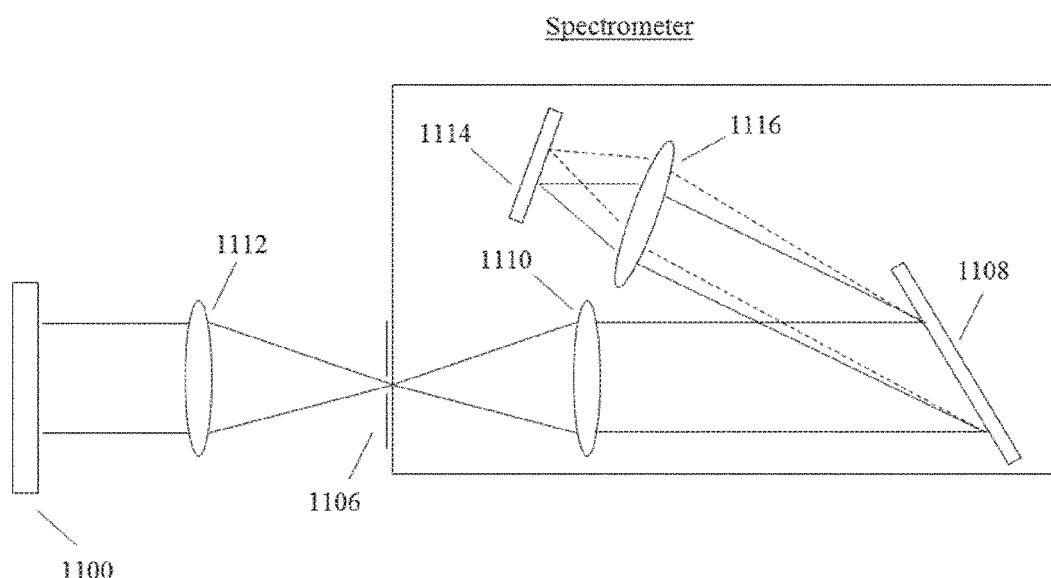
FIG. 11(b) shows a side view of the high-efficiency interferometer of FIG. 11(a)

An alternative embodiment to the one in FIG. 8 is depicted in FIGS. 11(a) and 11(b). In this embodiment shown from a top view in FIG. 11(a) and from the side view in FIG. 11(b), high-efficiency interferometer design including beamsplitter (1100) is used to maximize both the power to the sample and the collected light from the sample (1120). In a traditional setup e.g. FIG. 8, the collected light passes through the beamsplitter (807) twice (once during illumination and once during collection). For a 50/50 beamsplitter, 75% of the light is thus lost (50% for each pass). In some instances, a different splitting ratio such as 90/10 can be utilized to illuminate with 10% of the source and collect 90% of the backscattered light from the sample (see for example, Shemonski, N. D., et al, "Computational high-resolution optical imaging of the living human retina." Nature Photonics 9, 440-443, 2015), but an uneven splitting ratio where a small amount of light is directed to the sample typically makes sense when the total amount of light incident on the sample needs to be limited.

For a line-field system, a much higher total power can be incident on the sample, meaning that diverting less light to the sample is not ideal. In the configuration shown in FIGS. 11(a) and 11(b), most of the input light, e.g. 90% or even 99% can be directed to the sample (1120), then backscattered light from the sample bypasses the beamsplitter (1100) possibly through an aperture in a plane conjugate (or close to conjugate) to a Fourier plane relative to the sample. The beam directed to the sample 1120 is denoted by 1105a and a single plane-wave of the backscattered light collected from the sample 1121) is denoted by 1105b. This plane in the optical system, and its imaging conjugates, are referred to as 'Fourier planes' where the spatial distribution of light corresponds to the angular distribution of light in the sample plane at best focus. In a simplified optical system where the best focused plane in the sample lies at the front focal plane of an imaging lens, this Fourier plane lies at the back focal plane of the same lens. The reference beam (1102) first transmits through the beam splitter then reflects off a mirror (1103) and then is reflected off the beamsplitter (1100) on return. Since the collected sample light and the reference beam are spatially separated in the Fourier plane, a linear phase ramp will be introduced between the sample and reference in a plane conjugate to the sample (e.g. 1104). Due to the phase ramp, the interference fringes along the line of illumination will be modulated with a carrier frequency and can thus be used to remove one or more of the following: conjugate mirror image, autocorrelation signal, and need for background subtraction (see for example, US Patent Publication No. 2014/0028974).

When designing such a system for ophthalmic imaging, it might be desirable to place the pupil of the eye at or near to a plane conjugate to the beamsplitter (1100). In a design such as that depicted in FIG. 11(a), this means that the illumination and collection light are spatially separated on the pupil. To minimize the required size of the pupil and to make alignment with the subject easier it is desirable to minimize the distance between the illumination and collection beams. This can be taken to the extreme where the illumination and collection beams are again overlapped as in a traditional on-axis OCT system. To still efficiently remove the mirror image, autocorrelation signal, and the background signal, the reference arm can be offset using mirrors, lenses, or other optics causing the returning reference beam to not strike exactly the same place on the beamsplitter where it was divided (see for example, Fechtig, D. J., Grajciar, B., Schmoll, T., Blatter, C., Werkmeister, R. M., Drexler, W., & Leitgeb, R. A. (2015). Line-field parallel swept source MHz OCT for structural and functional retinal imaging. *Biomedical optics express*, 6(3), 716-735). The optics in the reference arm can also cause the reference beam to fully bypass the beamsplitter resulting in a setup similar to a Mach-Zehnder interferometer. Utilizing the aforementioned approaches effectively decouple the off-axis detection angle from the beam separation in the pupil of the eye. This also applies to non-ophthalmic systems where an aperture exists near a plane conjugate to the Fourier plane of the sample.

In order to use a system as diagramed in FIGS. 11(a) and (b) to image a human retina, the sample optics would be modified to image the aperture plane (containing the high efficiency beamsplitter) to the pupil of the human eye, and allow the optics of the eye to focus the light onto the retina, and the length of the reference arm would be increased to match the full optical length to the retina. One way the sample arm optics can be simply realized is to add an objective lens in the sample path forming a 4-f optical system where the distance between the imaging lens and the objective lens forms a Badal optometer, which can compensate for the refractive error of the patient by making small adjustments to the distance between the two lenses. The footprint in the pupil of the eye is an image of the aperture stop of the system containing the high efficiency beamsplitter, so the pupil of the eye can be thought of as an illumination pupil and an adjacent collection pupil.

A side-view of a portion of the system in FIG. 11(a), including the spectrometer, is shown in FIG. 11(b) where the Fourier plane relative to the sample on the beamsplitter (1100) is relayed (via optics 1110 and 1112) to the diffraction grating (1108). The grating can be of the reflective or transmissive type. An optional entrance slit (spatial filter, 1106) can be placed between these components. The diffracted light is then focused onto a 2D sensor 1114 (via optics 1116). Separate wavelengths will be spread along one dimension and spatial information along the other. This forms an imaging spectrometer.

Figure 12:
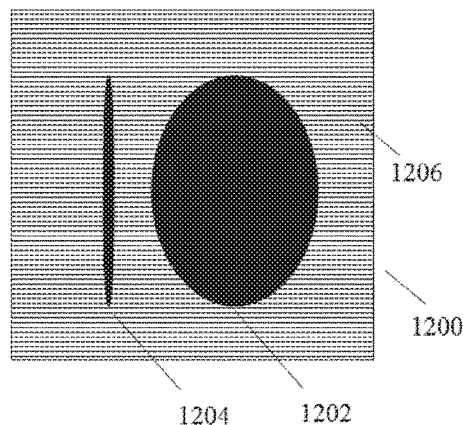
FIG. 12 illustrates an exemplary footprint of light when incident on a diffraction grating element of the interferometer in FIG. 11(b).

The footprint of light incident on the grating is as indicated in FIG. 12. The sample and reference beams are spatially separated by the aperture at the Fourier plane relative to the sample, and are thus separated on the grating where the reference beam footprint at the grating is denoted 1204 and the sample beam footprint at the grating is denoted 1202 (the grating is conjugate, or near conjugate, to a Fourier plane relative to the sample). When propagated to the sample plane (from the grating, through a lens, onto the sensor), the separation will result in a linear phase ramp between the reference and sample light.

The elliptical-shape to the sample beam profile (1202) is purposeful to indicate the possibility of such a profile. The origin of such a profile may arise from two separate phenomenon. First, the laser may produce an elliptical beam due to different divergence angles along orthogonal dimensions. For various reasons such as eye pupil dimensions, the FOV on the retina, cost, compactness, etc., it may be desirable to keep such an elliptical profile. Second, even when provided with a circular sample beam profile, gratings are typically tilted resulting in elliptical beam profiles incident on the grating. Although drawn such that the major axis of the sample beam ellipse is orthogonal to the grating grooves, such a design is not required, and it may be desirable to have the major axis parallel to the grooves (1206).

Compact Spectrometer

Figure 13A:
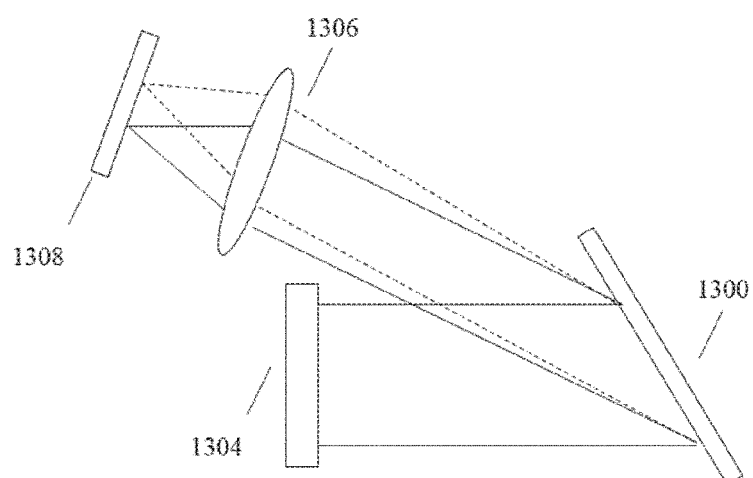
FIG. 13(a) is a side view of an example compact spectrometer design.
Figure 13B:
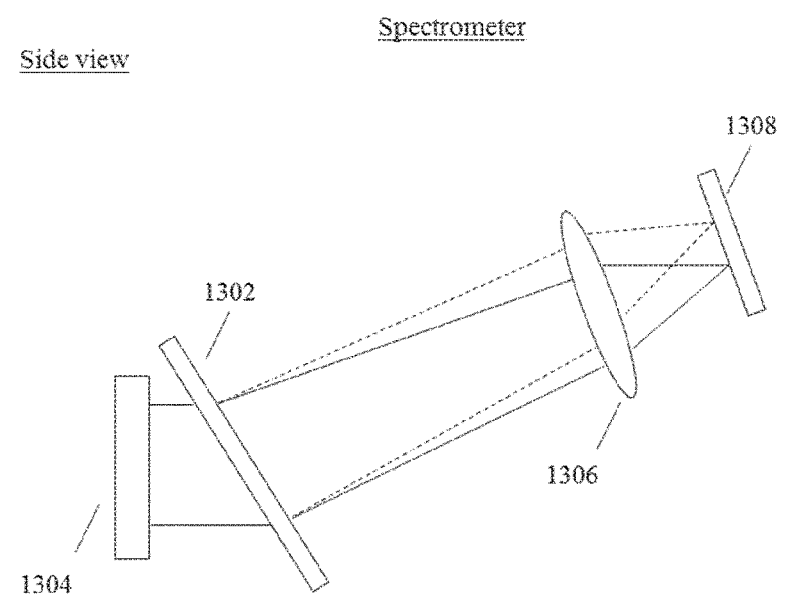

In FIG. 11(b), the beamsplitter (1100) is imaged (via two lenses, 1110 and 1112) to the grating (1108). This allowed for an optional entrance slit or spatial filter (1106). It might not be necessary to include such a slit or filter. In such an embodiment, spectrometer designs as depicted in FIGS. 13(a) and 13(b) could be employed. Here, the diffraction grating (reflective in FIG. 13(a), indicated by reference numeral 1300, and transmissive in FIG. 13(b), indicated by reference numeral 1302) is placed near the beamsplitter (1304). Similar to in the embodiment in FIG. 11(b), an optical element (1306) and 2D sensor (1308) would complete the imaging spectrometer. This eliminates the need for the two imaging lenses (1110 and 1112) in FIG. 11(b), but does not allow for the optional spatial filter (1106). With a careful optical design, strong back reflections from optical components could be eliminated resulting in an attractive design. Not only are the designs in FIGS. 13(a) and 13(b) much more compact than the design in FIG. 11(b), but they are also less expensive. Such compact spectrometers would be compatible with both double-pass and high-efficiency interferometric setups as described above in Sections "Use of Pulse Tuned Source in a Double-pass Interferometric System" and "Use of Pulse Tuned Source with a High-efficiency Interferometer"

In the situation where the grating must be separated away from the beamsplitter (such as might be the case in FIG. 13(a) and FIG. 13(b)), the grating and the beamsplitter need not be both placed in a Fourier plane of the camera. The spectral and spatial resolution may be compromised depending on the setup. In one embodiment, the beamsplitter is placed in a Fourier plane of the camera to maintain high spatial resolution. This ensures the camera is in a plane conjugate to the sample. Furthermore, because the incident beam on the grating is collimated along the dimension in which the spectrum is dispersed, after the grating, the collimated beams of different wavelengths would still be focused on the camera plane. The spectral resolution may only be slightly compromised due to different incident angles of different wavelengths (i.e. the setup is non-telecentric along the spatial dimension). In another embodiment, the grating is in a Fourier plane of the camera to achieve high spectral resolution; however the sample may be defocused along the orthogonal (spatial) dimension. To avoid a loss of resolution in this dimension due to defocus blurring, computational refocusing in this dimension could bring the sample back into focus. Using techniques such as holoscopy (see for example, US Publication No. 2014/0028974) along the one spatial dimension, optimal resolution could be recovered. In yet another embodiment, two cylindrical lenses of different focal lengths could be employed such that both the spatial and spectral dimensions are optimally focused on the camera plane without loss of spatial and spectral resolution. Implementation of various optical elements, for example, focusing grating or grism, may further reduce the size of the spectrometer and would be recognized by those skilled in the art upon reading the teachings herein.

Self-Interference Interferometry

Self-interference or self-referenced interferometry is a configuration where there may be additional synergies with special applications of a source of the present application. Self-referenced interferometry is a depth resolved interferometric technique, very similar to OCT, wherein the 'reference light' originates in, or on the sample itself, rather than in an explicitly defined reference arm which is part of the imaging system. For example, a self-interface interferometer can be the system of FIG. 8 without the reference arm. The reconstructed depth can be optimally thin if the reference surface is in contact with, or in a portion of the sample of interest. Self-interference interferometry has the additional advantage where axial motion of the imaged object tends to move all interfering scatterers in unison, and therefore does not cause axial motion induced phase washout. In this case, the integration and sweep time can be increased up to the point where lateral motion of the sample becomes a limiting factor. Longer integration times may enable sensing by a slower rate detector array and enable delivery of more energy in a single acquisition. Because lateral alignment between the interfering portions of the beam is inherent, self-interference interferometry is also tolerant to spatially multimode lasers.

Although self-interference interferometry is compatible with previous system configurations such as the double-pass interferometer, high-efficiency interferometer, 2-D spectrometer, and compact spectrometer (with a simple blocking of the explicit reference path), other configurations are also uniquely possible with this modality. Applications requiring small imaging depths require less spectral resolution at the detector. In cases where the imaging depth required is very thin (one of which is self-interference interferometry), the pulse tuned diode may be used directly as a swept source in a traditional time resolved detecting scenario. Instead of a 2D spectrometer as described in the hybrid SS/SD-OCT solutions above, a fast array detector (either linear or 2D) is used in this case to resolve the swept spectrum as a temporal series, with relatively poor spectral resolution. This configuration simplifies the optical configuration of the system. It does, however require relatively fast electronics, which may be frequently idle, as the source requires a low duty cycle during the measurement period.

Sources which are spatially multimode will not interfere with high contrast if an attempt is made to interfere spatially distinct regions of the field with each other. Spatially multimode sources are more difficult to manage than spatially single mode sources when illuminating an area. Although the multiple modes may illuminate the sample and are transmitted to the detector, the difficulty arises because the reference arm must accurately align the same spatial modes to overlap on the detector. A special case where alignment is inherently maintained is self-interference interferometry. Spatially multimode sources which tolerate very high current (such as SPL PL85 OSRAM Opto Semiconductors, GmbH) are designed for laser range finders and are available at a variety of wavelengths in the infrared wavelength region. These sources can additionally be low cost because the pulsed driver is available integrated into the packaging and require only a low voltage DC voltage drive. Laser range finders have traditionally operated around 850, 920, and 1064 nm. For low cost applications in the near future, the large consumer application of the diode laser will define the available wavelengths.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

The foregoing description of the embodiments of the present subject matter has been presented for the purposes of illustration and description. It is not intended to be exhaustive or to limit the present embodiment of subject matter to the precise form disclosed. Many modifications and variations are possible in tight of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof.

The invention claimed is:

1. An optical system for imaging a sample comprising:
   a diode laser having a junction for providing a beam of radiation, said diode laser having a first spectral output bandwidth when driven under constant current conditions;

a driver circuit to apply a pulse of drive current to the diode laser, said pulse having a current amplitude that varies in time causing a variation in the output wavelength of the diode laser during the pulse to produce a second spectral output bandwidth that is at least two times larger than the first spectral output bandwidth under constant current conditions, the second spectral output bandwidth being characterized by a region of resonant peaks distinct from a region of smoother spectrum;

a beam divider for dividing the beam of radiation into a sample arm and a reference arm, wherein the sample arm contains the sample to be imaged;

a detector to measure in the spectral domain an interference of a sample beam returning from the sample arm and a reference beam returning from the reference arm; and a processor to convert the measured interference into depth information of the sample;

wherein the system attenuates the region of resonant peaks so that the beam is dominated by the region of smoother spectrum.

2. The system of claim 1, wherein the processor implements a windowing function to attenuate the region of resonant peaks.

3. The system of claim 1, wherein the rate of change of the current amplitude of the pulse is slow enough such that the difference between the actual temperature of the junction and the equilibrium temperature of the junction is minimized during the pulse.

4. The system of claim 1, wherein:
the beam divider is substantially at the Fourier plane, or conjugate to the Fourier plane, of the sample; and
the sample beam returning from the sample arm passes through the same Fourier or conjugate plane and bypasses the beam divider.

5. The system of claim 4, wherein the reference beam returning from the reference arm passes through the same Fourier or conjugate plane and is spatially separated at the Fourier or conjugate plane from the sample beam returning from the sample arm.

6. An optical coherence tomography (OCT) system for imaging a sample comprising:
a radiation source for providing a beam of radiation;
a beam divider for dividing the beam of radiation into a sample arm and a reference arm,
optics in the sample arm to focus the beam of radiation onto the sample to be imaged;
a detector to measure interference of the beams returning from the sample and reference arms; and
a processor to convert the measured interference into depth information of the sample;
wherein:
the beam divider is substantially at the Fourier plane, or conjugate to the Fourier plane, of the sample;
a sample beam returning from the sample arm passes through the same Fourier, or conjugate, plane and bypasses the beam divider, and wherein the radiation source includes a diode laser having a junction for providing a beam of radiation, said diode laser having a first spectral output bandwidth when driven under constant current conditions, said system including:
a driver circuit to apply a pulse of drive current to the diode laser, said pulse having a current amplitude that varies in time causing a variation in the output wavelength of the diode laser during the pulse to produce a second spectral output bandwidth that is at least two times larger than the first spectral output bandwidth under constant current conditions, the second spectral output bandwidth being characterized by a region of resonant peaks distinct from a region of smoother spectrum; and
wherein the system attenuates the region of resonant peaks so that the beam of radiation is dominated by the region of smoother spectrum.

7. The system of claim 6, wherein a reference beam returning from the reference arm passes through the same Fourier or conjugate plane and is spatially separated at the Fourier or conjugate plane from the sample beam returning from the sample arm.

8. The system of claim 6,
wherein the rate of change of the current amplitude of the pulse is slow enough such that the difference between the actual temperature of the junction and the equilibrium temperature of the junction is minimized during the pulse.

* * * * *

UNITED STATES PATENT AND TRADEMARK OFFICE
CERTIFICATE OF CORRECTION

PATENT NO. : 10,809,050 B2
APPLICATION NO. : 16/669289
DATED : October 20, 2020
INVENTOR(S) : Alexandre R. Tumlinson et al.

Page 1 of 3

It is certified that error appears in the above-identified patent and that said Letters Patent is hereby corrected as shown below:

On the Title Page

In item (57), in Column 2, in "Abstract", Line 10, delete "larger" and insert -- larger than --, therefor.

In the Specification

In Column 1, Line 23, delete "Observed" and insert -- observed --, therefor.

In Column 1, Lines 52-53, delete "distributed." and insert -- distributed --, therefor.

In Column 1, Line 64, delete "lens." and insert -- 1 ms. --, therefor.

In Column 2, Line 2, delete "B," and insert -- B. --, therefor.

In Column 2, Line 59, delete "STD," and insert -- SLD. --, therefor.

In Column 5, Lines 3-5, delete "FIG. 2(a) shows a plot of the output power vs. current of the diode laser. FIG. 2(b) shows a plot of the wavelength vs. temperature of the diode laser." and insert the same on Column 5, Line 2, as continuation of the same paragraph.

In Column 5, Line 7, delete "10 ms," and insert -- 10 ms. --, therefor.

In Column 5, Line 40, delete "11(a)" and insert -- 11(a). --, therefor.

In Column 5, Line 55, delete "entirely." and insert -- entirety. --, therefor.

In Column 5, Line 59, delete "ma" and insert -- may --, therefor.

In Column 7, Line 15, delete "detector," and insert -- detector. --, therefor.

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,809,050 B2

In Column 7, Line 28, delete "hut" and insert -- but --, therefor.

In Column 7, Line 30, delete "Full field" and insert -- Full-field --, therefor.

In Column 7, Line 60, delete "signals," and insert -- signals. --, therefor.

In Column 8, Line 42, delete "succession" and insert -- succession. --, therefor.

In Column 8, Line 47, delete "and." and insert -- and --, therefor.

In Column 8, Line 55, delete "fight" and insert -- light --, therefor.

In Column 9, Line 49, delete "valued." and insert -- valued --, therefor.

In Column 9, Line 52, delete "B-scam)" and insert -- B-scan) --, therefor.

In Column 9, Line 62, delete "M" and insert -- in --, therefor.

In Column 11, Line 46, after "include" insert -- a --.

In Column 12, Line 36, delete "Line" and insert -- line --, therefor.

In Column 12, Line 39, delete "shill" and insert -- shift --, therefor.

In Column 12, Lines 51-52, delete "wavelength," and insert -- wavelength. --, therefor.

In Column 13, Line 15, delete "tow" and insert -- low --, therefor.

In Column 13, Line 23, delete "vs," and insert -- vs. --, therefor.

In Column 13, Line 45, delete "current," and insert -- current. --, therefor.

In Column 13, Line 63, delete "702," and insert -- 702. --, therefor.

In Column 14, Line 1, delete "wilt" and insert -- will --, therefor.

In Column 14, Line 49, delete "FIG. 1)" and insert -- FIG. 1). --, therefor.

In Column 14, Line 59, delete "Segref" and insert -- Segref, --, therefor.

In Column 14, Line 61, delete "93120N-93120N), international" and insert -- 93120N-93120N). International --, therefor.

In Column 14, Line 66, after "Boer," insert -- J., --.

In Column 15, Line 4, delete "Frisker," and insert -- Frisken, --, therefor.

CERTIFICATE OF CORRECTION (continued)
U.S. Pat. No. 10,809,050 B2

In Column 15, Line 5, delete "BIOS" and insert -- BiOS --, therefor.

In Column 15, Line 11, delete "Itch," and insert -- Itoh, --, therefor.

In Column 15, Line 19, delete "6(13)," and insert -- 6(3), --, therefor.

In Column 15, Line 21, delete "(2010)," and insert -- (2010). --, therefor.

In Column 15, Line 23, delete "Fall" and insert -- full --, therefor.

In Column 15, Line 37, delete "lens" and insert -- 1 ms --, therefor.

In Column 15, Line 39, before "Leitgeb," insert -- & --.

In Column 16, Line 60, delete "arc" and insert -- are --, therefor.

In Column 17, Line 9, delete "detector," and insert -- detector. --, therefor.

In Column 17, Line 32, delete "FIG. 10(b) in" and insert -- FIG. 10(b). In --, therefor.

In Column 17, Line 56, delete "(tar" and insert -- (for --, therefor.

In Column 18, Line 5, delete "detector," and insert -- detector. --, therefor.

In Column 18, Line 11, delete "spectrum" and insert -- spectrum. --, therefor.

In Column 18, Line 35, delete "space," and insert -- space. --, therefor.

In Column 18, Line 37, delete "sine," and insert -- sinc, --, therefor.

In Column 18, Line 46, delete "interpolation)," and insert -- interpolation). --, therefor.

In Column 18, Line 57, before "high-efficiency" insert -- a --.

In Column 18, Line 67, delete "al," and insert -- al. --, therefor.

In Column 19, Line 16, delete "1121)" and insert -- 1120 --, therefor.

In Column 19, Line 51, delete "(sec" and insert -- (see --, therefor.

In Column 21, Line 6, delete "Interferometer""" and insert -- Interferometer". --, therefor.

In Column 22, Line 54, delete "tight" and insert -- light --, therefor.